US010392593B2

(12) United States Patent
Kasuto et al.

(10) Patent No.: US 10,392,593 B2
(45) Date of Patent: Aug. 27, 2019

(54) SYSTEMS AND METHODS FOR GROWING AND HARVESTING CELLS

(71) Applicant: Pluristem Ltd., Haifa (IL)

(72) Inventors: Harel Kasuto, Kibbutz Yifat (IL); Ohad Karnieli, Tivon (IL); Dotan Hoffman, Haifa (IL); Lior Raviv, Ra'anana (IL)

(73) Assignee: PLURISTEM LTD., Haifa (IL)

( * ) Notice: Subject to any disclaimer, the term of this patent is extended or adjusted under 35 U.S.C. 154(b) by 202 days.

(21) Appl. No.: 15/123,616

(22) PCT Filed: Mar. 3, 2015

(86) PCT No.: PCT/IB2015/051559
§ 371 (c)(1),
(2) Date: Sep. 2, 2016

(87) PCT Pub. No.: WO2015/132729
PCT Pub. Date: Sep. 11, 2015

(65) Prior Publication Data
US 2017/0073625 A1    Mar. 16, 2017

Related U.S. Application Data

(60) Provisional application No. 61/947,455, filed on Mar. 4, 2014.

(51) Int. Cl.
| | |
|---|---|
| *C12M 1/00* | (2006.01) |
| *C12M 1/06* | (2006.01) |
| *C12M 1/12* | (2006.01) |
| *C12M 1/34* | (2006.01) |
| *C12M 1/36* | (2006.01) |

(Continued)

(52) U.S. Cl.
CPC ............ *C12M 23/34* (2013.01); *C12M 25/14* (2013.01); *C12M 25/16* (2013.01); *C12M 27/02* (2013.01); *C12M 27/10* (2013.01); *C12M 27/16* (2013.01); *C12M 41/12* (2013.01); *C12M 41/26* (2013.01); *C12M 41/48* (2013.01); *C12M 47/02* (2013.01); *C12N 5/0075* (2013.01)

(58) Field of Classification Search
CPC ...... C12M 23/34; C12M 25/14; C12M 25/16; C12M 27/10; C12M 47/02; C12M 27/02; C12M 27/16; C12M 41/48; C12M 41/26; C12M 41/12; C12N 5/0075
See application file for complete search history.

(56) References Cited

U.S. PATENT DOCUMENTS 4,885,137 A * 12/1989 Lork ................. B01J 8/226
                                                                422/140
5,081,036 A *  1/1992 Familletti .......... C12M 29/08
                                                                435/286.7
(Continued)

FOREIGN PATENT DOCUMENTS

| EP | 0365313 A2 | 4/1990 |
|---|---|---|
| WO | WO 2005/044972 A2 | 5/2005 |

(Continued)

*Primary Examiner* — Gautam Prakash
(74) *Attorney, Agent, or Firm* — Lando & Anastasi, LLP

(57) ABSTRACT

This disclosure is directed to methods and systems for growing and/or harvesting cells. The method can include seeding cells on a plurality of carriers. The method can also include incubating the carriers under conditions suitable for cell growth.

15 Claims, 26 Drawing Sheets

(51) Int. Cl.
*C12M 3/04* (2006.01)
*C12M 3/06* (2006.01)
*C12N 5/00* (2006.01)

(56) References Cited

U.S. PATENT DOCUMENTS

| | | | |
|---|---|---|---|
| 5,187,095 | A | 2/1993 | Bliem et al. |
| 5,501,971 | A | 3/1996 | Freedman et al. |
| 6,911,201 | B1 | 6/2005 | Merchav et al. |
| 7,534,609 | B2 | 5/2009 | Merchav et al. |
| 7,678,573 | B2 | 3/2010 | Merchav et al. |
| 8,524,496 | B2 | 9/2013 | Meiron et al. |
| 8,529,888 | B2 | 9/2013 | Meiron et al. |
| 9,096,827 | B2 | 8/2015 | Meiron et al. |
| 9,393,273 | B2 | 7/2016 | Meiron |
| 9,512,393 | B2 | 12/2016 | Kasuto et al. |
| 2005/0176143 | A1 | 8/2005 | Merchav et al. |
| 2005/0181504 | A1 | 8/2005 | Merchav et al. |
| 2009/0004738 | A1 | 1/2009 | Merchav et al. |
| 2010/0209403 | A1 | 8/2010 | Meiron et al. |
| 2011/0129447 | A1 | 6/2011 | Meretski et al. |
| 2011/0129486 | A1 | 6/2011 | Meiron |
| 2011/0171182 | A1 | 7/2011 | Meiron et al. |
| 2011/0256108 | A1 | 10/2011 | Meiron et al. |
| 2011/0256159 | A1 | 10/2011 | Meiron et al. |
| 2011/0256160 | A1 | 10/2011 | Meiron et al. |
| 2011/0293583 | A1 | 12/2011 | Aberman |
| 2012/0122220 | A1 | 5/2012 | Perski et al. |
| 2013/0004465 | A1 | 1/2013 | Aberman |
| 2013/0039892 | A1 | 2/2013 | Aberman |
| 2013/0259843 | A1 | 10/2013 | Duda et al. |
| 2013/0323213 | A1 | 12/2013 | Meiron et al. |
| 2013/0337558 | A1 | 12/2013 | Meiron et al. |
| 2014/0017209 | A1 | 1/2014 | Aberman et al. |
| 2014/0030805 | A1 | 1/2014 | Kasuto et al. |
| 2014/0242039 | A1 | 8/2014 | Meiron et al. |
| 2015/0125138 | A1 | 5/2015 | Duda et al. |
| 2015/0216907 | A1 | 8/2015 | Chajut et al. |
| 2015/0232797 | A1 | 8/2015 | Kasuto et al. |
| 2016/0022738 | A1 | 1/2016 | Meretski et al. |
| 2016/0058799 | A1 | 3/2016 | Aberman |
| 2016/0186259 | A1 | 6/2016 | Ofir et al. |
| 2016/0271184 | A1 | 9/2016 | Meiron |

FOREIGN PATENT DOCUMENTS

| | | |
|---|---|---|
| WO | WO 2012/140519 A2 | 10/2012 |
| WO | WO 2014/037862 A1 | 3/2014 |

\* cited by examiner

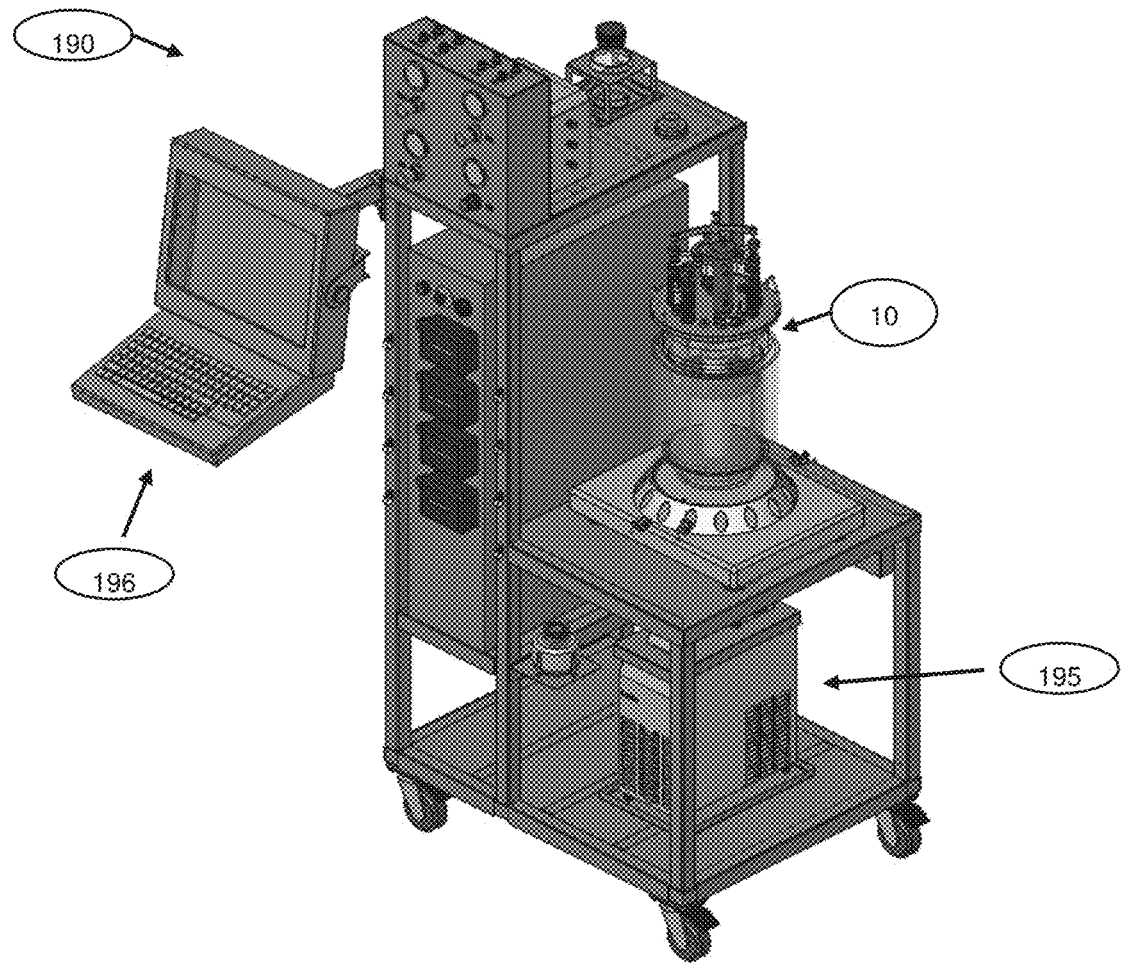

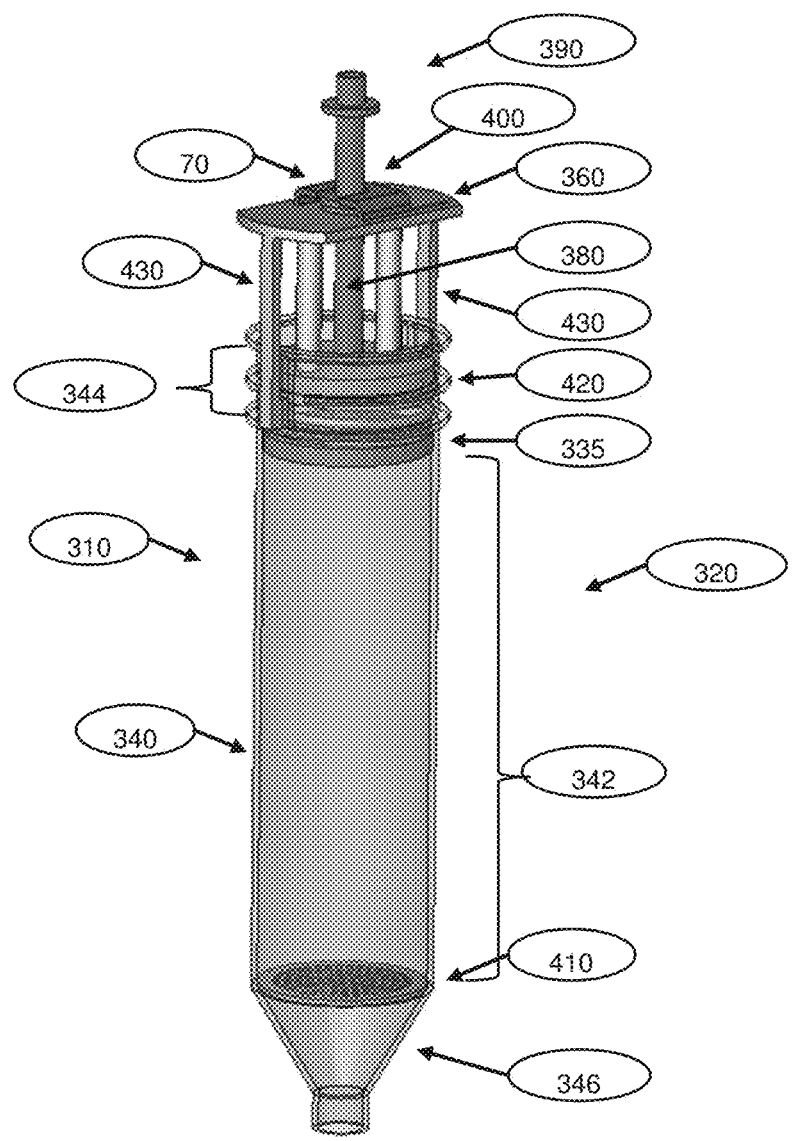

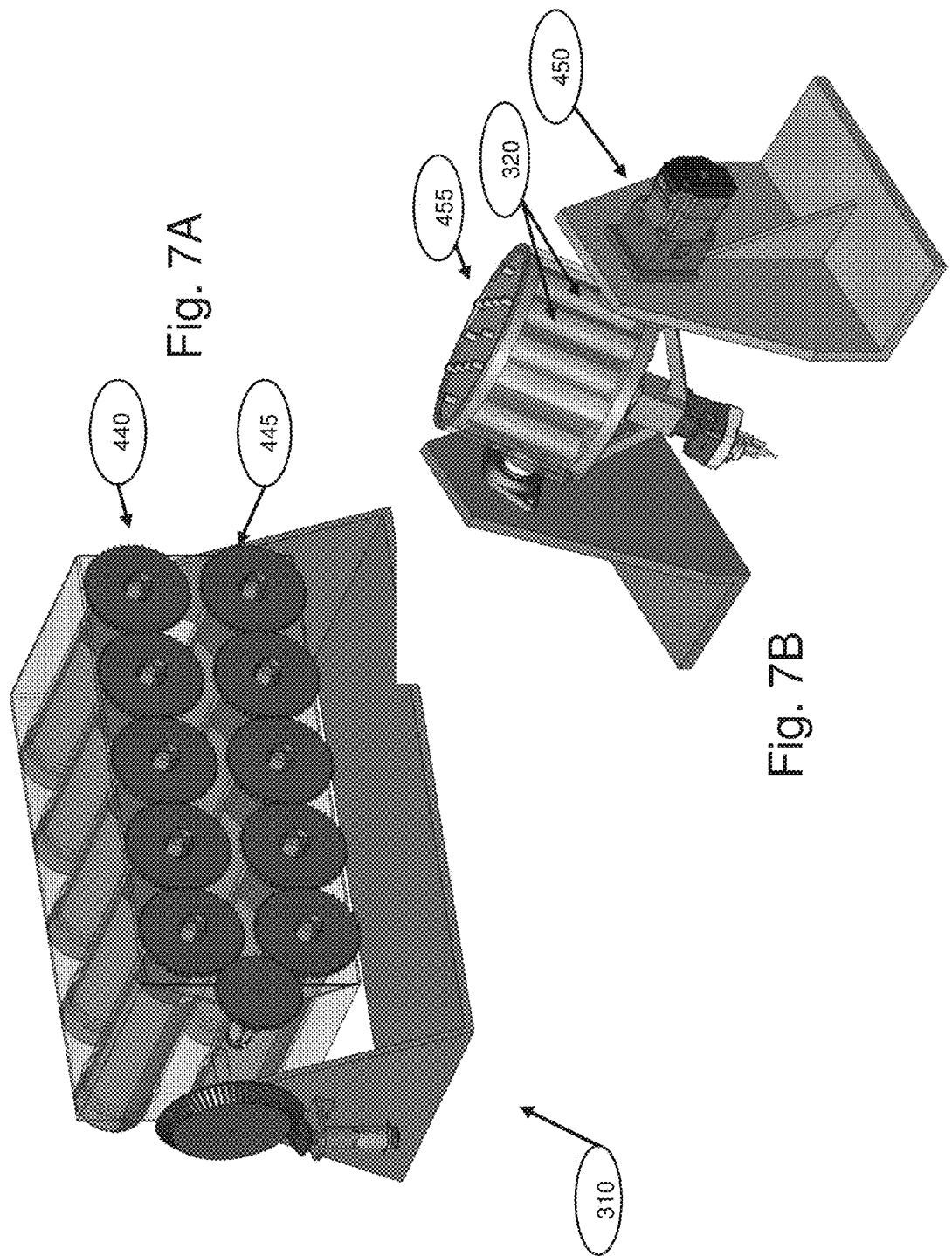

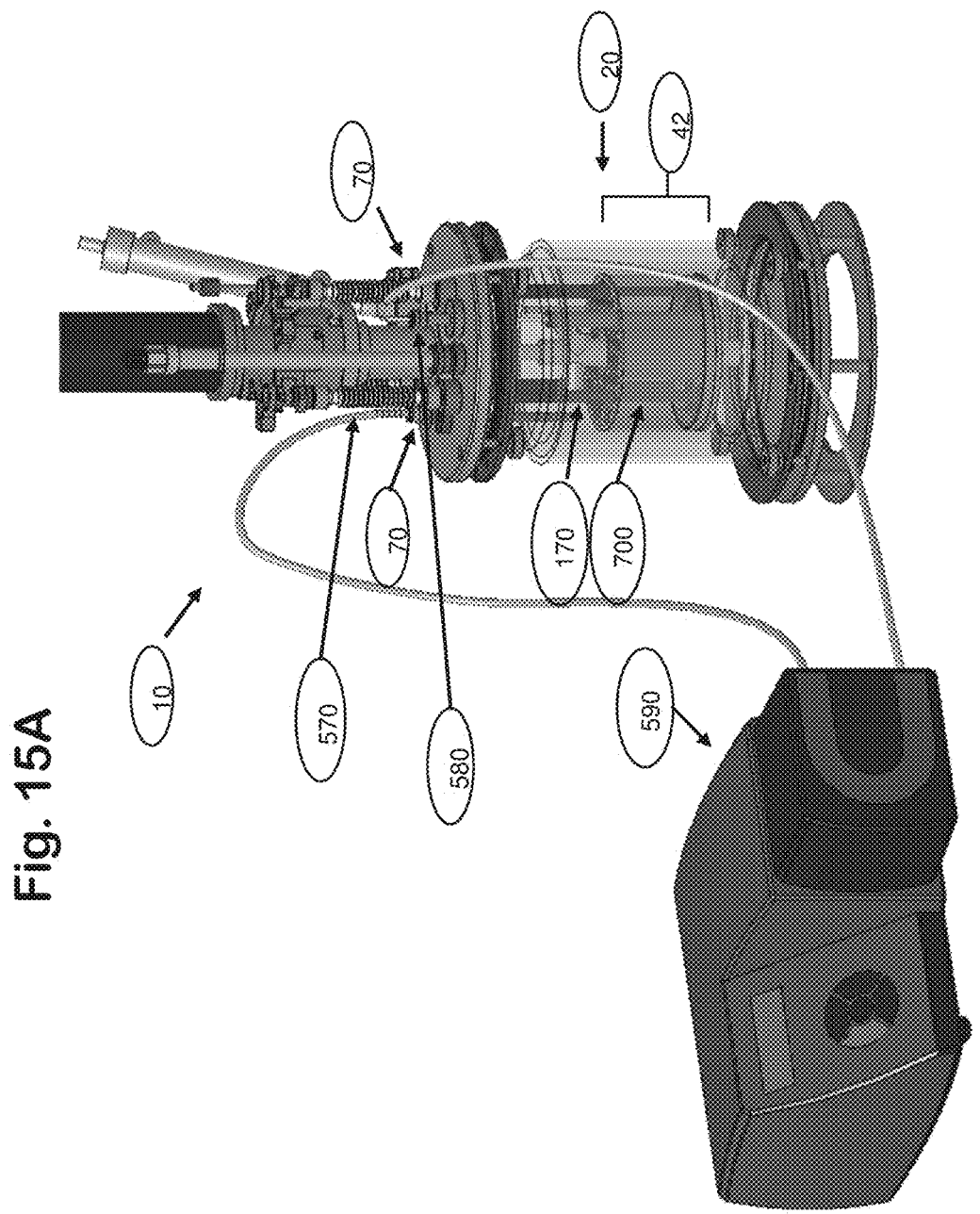

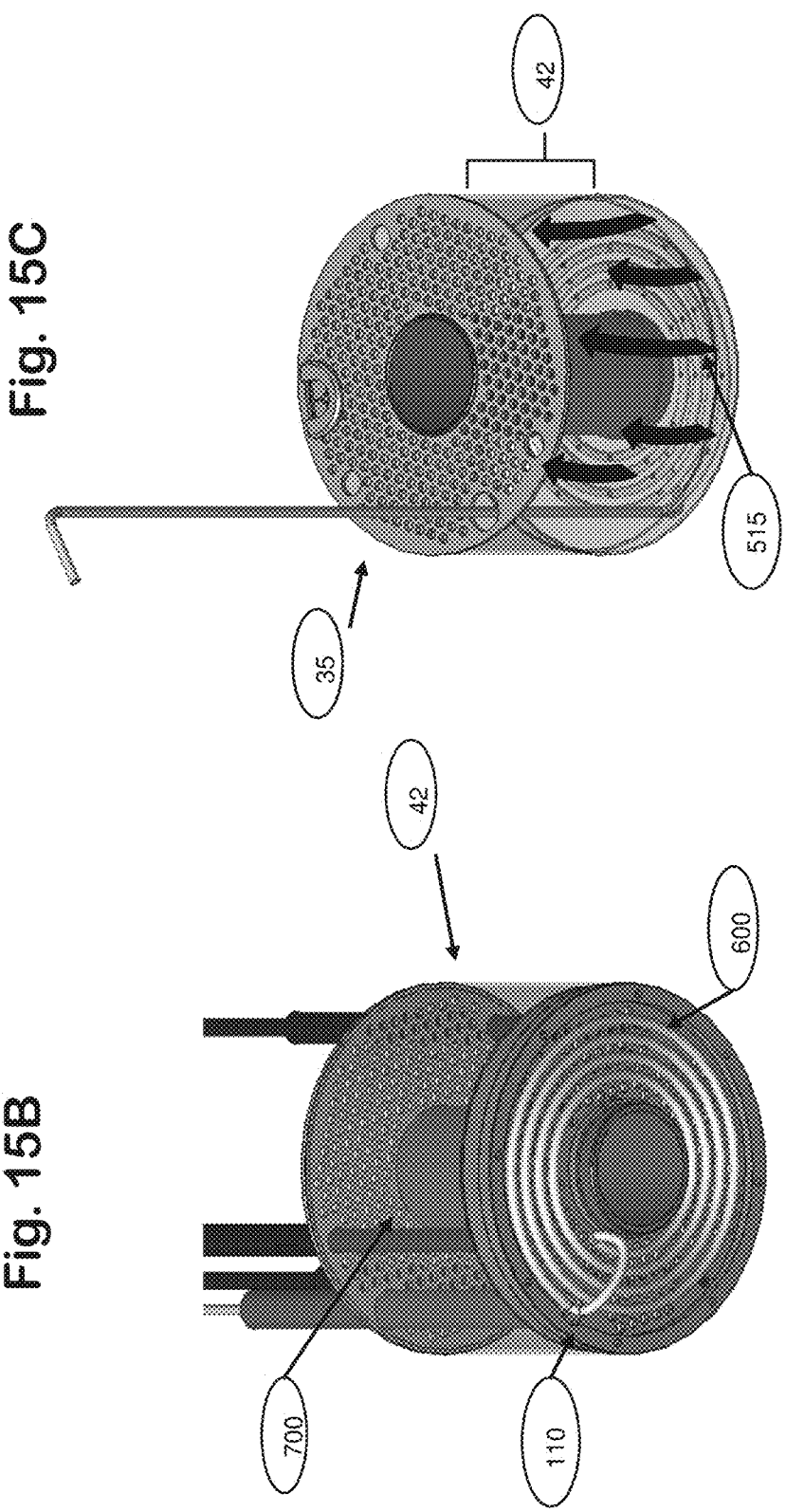

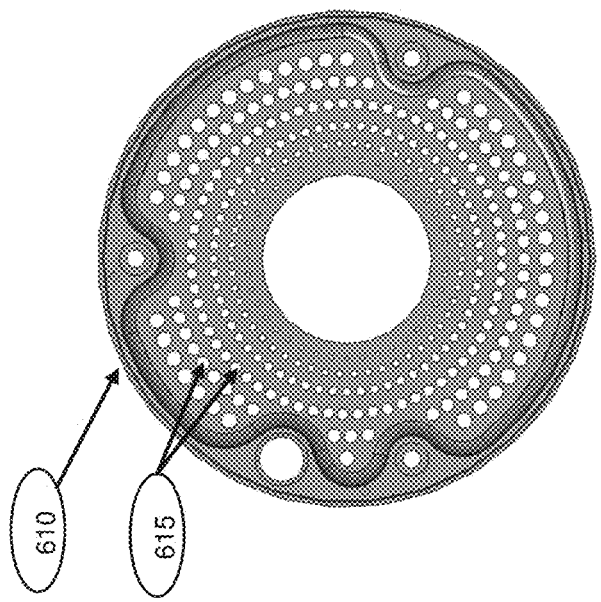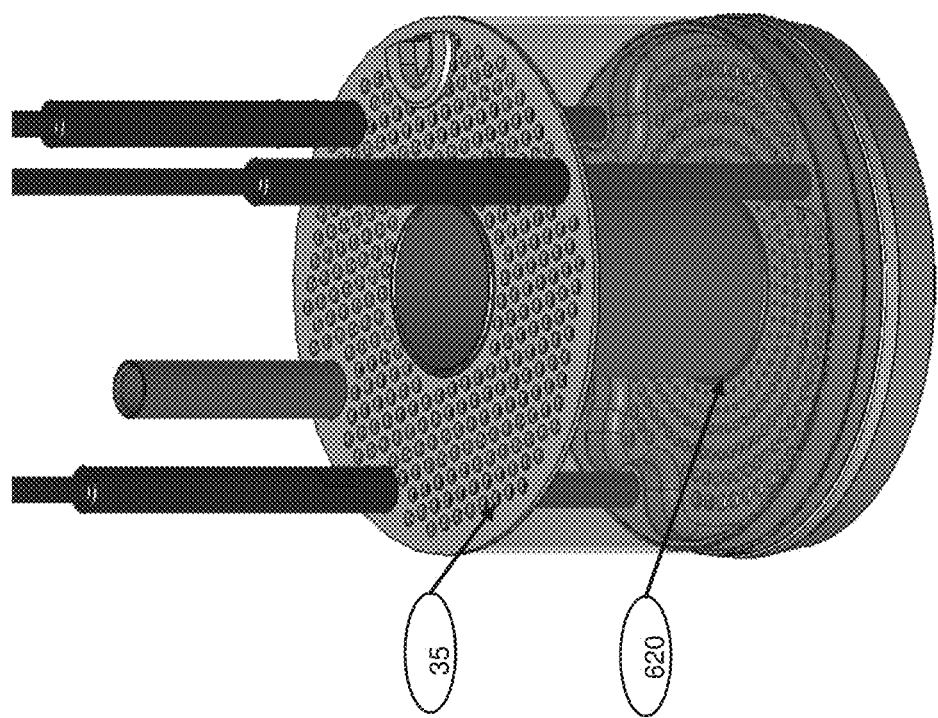

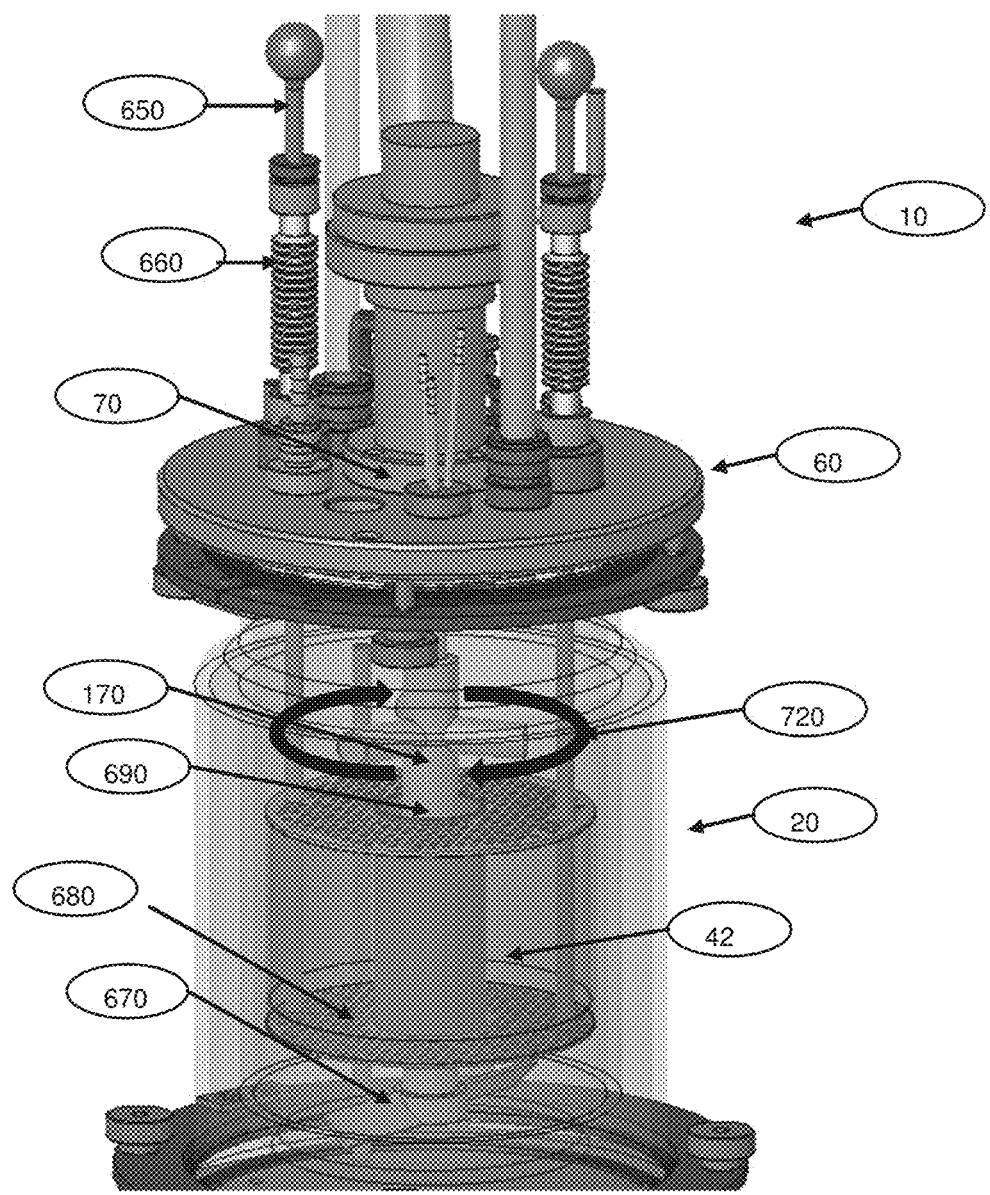

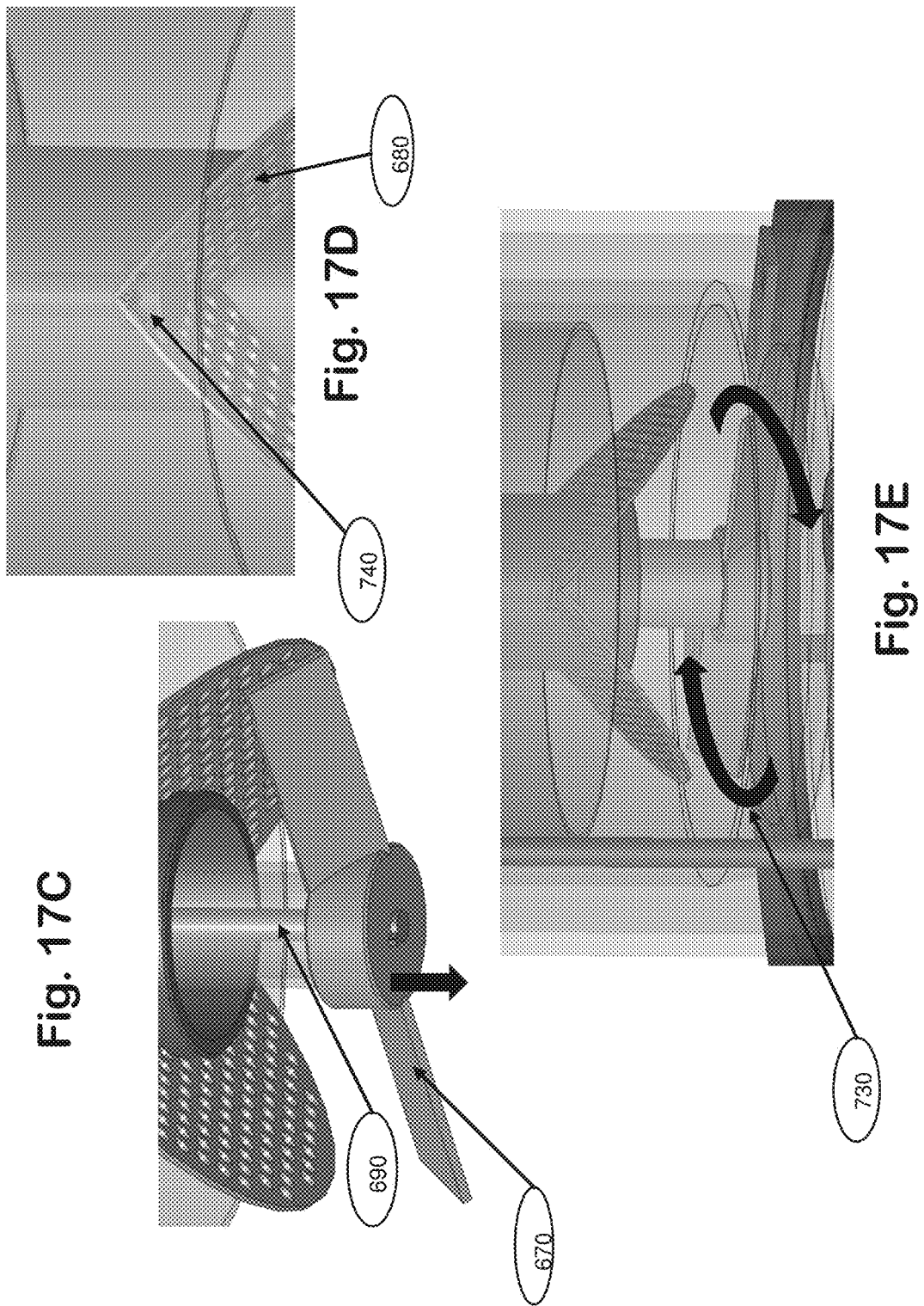

SYSTEMS AND METHODS FOR GROWING AND HARVESTING CELLS

RELATED APPLICATIONS

This application is a national stage filing under U.S.C. § 371 of PCT International Application PCT/IB2015/051559, filed Mar. 3, 2015, which claims priority under 35 U.S.C. § 119(e) to U.S. Provisional Application Ser. No. 61/947,455, entitled "SYSTEMS AND METHODS FOR GROWING AND HARVESTING CELLS" filed on Mar. 4, 2014, which are herein incorporated by reference in their entirety.

DESCRIPTION OF THE DISCLOSURE

Field of the Technology

The present disclosure relates to systems and methods for growing (proliferating) and/or harvesting cells.

Background

Various systems and methods have been developed to seed, grow, and harvest cells ex vivo. Numerous factors can affect these processes, including cell type, medium, and culturing conditions. Some cells grow well in suspension, while others require surface adherence for growth and division.

Eukaryotic cells, for example, are often grown in two-dimensional (2D) flasks or trays, such as the NUNCLON™ Δ CELL FACTORY, which can include stacks of cell culture flasks. While these systems can provide adequate growth under certain conditions, they are often unable to continuously monitor or control environmental parameters such as DO, pH, introduction of nutrients, or removal of waste products. In addition, these systems can suffer from low efficiency and/or low surface area to volume ratios, the need for labor-intensive manipulation of culture flasks, and long time periods for seeding and culture, which can be costly and detrimental to cell viability.

Some cell types may be grown in three-dimensional (3D) matrices. Such matrices can include porous, non-woven or woven fiber, and sponge-like materials that can be placed in a packed bed inside a bioreactor. These carriers are often used for the production and collection of secreted proteins, while the cells remain attached to the matrix, rather than for the culture of cells that are ultimately removed and used as therapeutic agents. Examples of such carriers are FIBRA-CELL® DISKS (New-Brunswick), and porous ceramic carriers.

As an alternative, cells may be cultured in a bioreactor using non-porous micro-carriers in suspension or in a fluidized bed. This method allows cell growth in a monolayer on the surface of micro-carriers. Using this method, however, often involves separation of carriers from media by sedimentation or filtration, which are not straightforward processes and may not result in high cell-recovery rates. Furthermore, micro-carriers have deviations in surfaces on a cellular scale, which results in a culture environment that is different from two-dimensional culture systems.

SUMMARY OF THE DISCLOSURE

Aspects of the disclosure relate to systems and methods that allow more efficient seeding and growth (proliferation) of cells (e.g., on 2D surfaces) and provide more efficient harvesting of these cells.

Traditional cell growth has included small-scale growth devices for growing cells in volumes less than about 100 ml, as are commonly used in laboratories growing small batches of cells. Large-scale growth typically involves volumes greater than about 100 ml, which are often used in industrial or commercial applications. Devices utilized can include tubes, flasks, bioreactors, and cell factories, typically ranging in size from several milliliters to more than one thousand liters.

These traditional devices can be limited in their scalability, control of growth parameters, possibility of external contamination, and ability to be automated. Additional limitations may include variation between vessels and incubations, and long processing times. Aspects of the systems, devices, and methods described herein can be used to supplement or replace existing technologies.

One embodiment consistent with the principles of this disclosure is a method of growing and harvesting cells, for example, in a manner that addresses deficiencies encountered with traditional devices. In some embodiments, methods provided herein can include seeding cells on a plurality of carriers and packing the plurality of carriers in a vessel to create a packed volume. The method can also include incubating the carriers under conditions suitable for cell growth and freeing the plurality of carriers from the packed volume to permit at least some of the carriers to move and contact other carriers. In some embodiments, the unpacking step is performed in the presence of a releasing agent, or after treatment with a releasing agent. Also provided is a bioreactor configured for any of the aforementioned methods.

Another embodiment of this disclosure is directed to a method for growing and harvesting cells. The method can include adding cells to a vessel containing a growth medium (hereinafter "medium" or "media") and a plurality of carriers packed within the vessel under conditions wherein the cells will adhere to the carriers, maintaining the adhered cells under conditions suitable for cell growth, and unpacking the plurality of carriers to permit release of viable cells into the medium.

Another embodiment of this disclosure is directed to a system for growing and harvesting cells. The system can include a vessel configured to receive a plurality of carriers, and a component located within the vessel, wherein the component can be moved from a first position configured to pack the plurality of carriers to a second position configured to permit movement of the plurality of carriers.

In other embodiments is provided a method of seeding cells in a bioreactor containing carriers, comprising the step of stirring the carriers during the seeding process. Also provided is a bioreactor configured for the aforementioned method.

In other embodiments is provided a method of seeding cells in a bioreactor containing carriers in a central "basket" region and a circulation device that creates a downward flow, utilizing a device dispersed at the bottom of the basket region, having pores that increase in size towards the periphery of the device. Alternatively or in addition, the method utilizes a device dispersed at the bottom of the basket region, having relatively small pores. Also provided are bioreactors comprising, in various embodiments, one or both of the aforementioned parts.

In other embodiments is provided a method of seeding cells in a bioreactor containing carriers in a central "basket" region, utilizing a device dispersed at the bottom of the basket region that can open, allowing the carriers to pass into a different compartment of the vessel, which is typically disposed adjacent to said device and is in some embodiments below the basket region. In certain embodiments, the carriers passively fall into the lower region. Alternatively or in addition, the method utilizes a propeller disposed in the different compartment. Also provided is a bioreactor comprising, in various embodiments, one or both of the aforementioned parts.

Additional embodiments consistent with principles of the disclosure are set forth in the detailed description which follows or may be learned by practice of methods or use of systems or articles of manufacture disclosed herein. It is understood that both the foregoing general description and the following detailed description are exemplary and explanatory only, and are not restrictive of the disclosure as claimed. Additionally, it is to be understood that other embodiments may be utilized and that electrical, logical, and structural changes may be made without departing form the spirit and scope of the present disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure. In the drawings:

FIG. 5A is a perspective view of a system under growth conditions, according to an exemplary embodiment.

FIG. 6 is a perspective view of a system for growing and harvesting cells, according to another exemplary embodiment.

FIG. 7A is a perspective view of an agitation device, according to an exemplary embodiment.

FIG. 7B is a perspective view of another agitation device, according to an exemplary embodiment.

FIG. 15A is a perspective view of a system for growing and harvesting cells in an opened position, according to another exemplary embodiment.

FIG. 15B is an inverted view of a middle region of the system of FIG. 15A.

FIG. 15C is a perspective view of a middle region of the system of FIG. 15A.

FIG. 16B is a cutaway view of a vessel of the system of FIG. 16A.

FIG. 16C is a top view of a lower component of the system of FIG. 16A.

FIG. 17A is a perspective view of a system for growing and harvesting cells in an opened position, according to another exemplary embodiment.

FIG. 17C is a perspective view of a propeller of the system of FIG. 17A.

FIG. 17D is a perspective view of a lower component of the system of FIG. 17A.

FIG. 17E is a perspective view of a lower section of the system of FIG. 17A.

DESCRIPTION OF THE EMBODIMENTS

Figure 1:
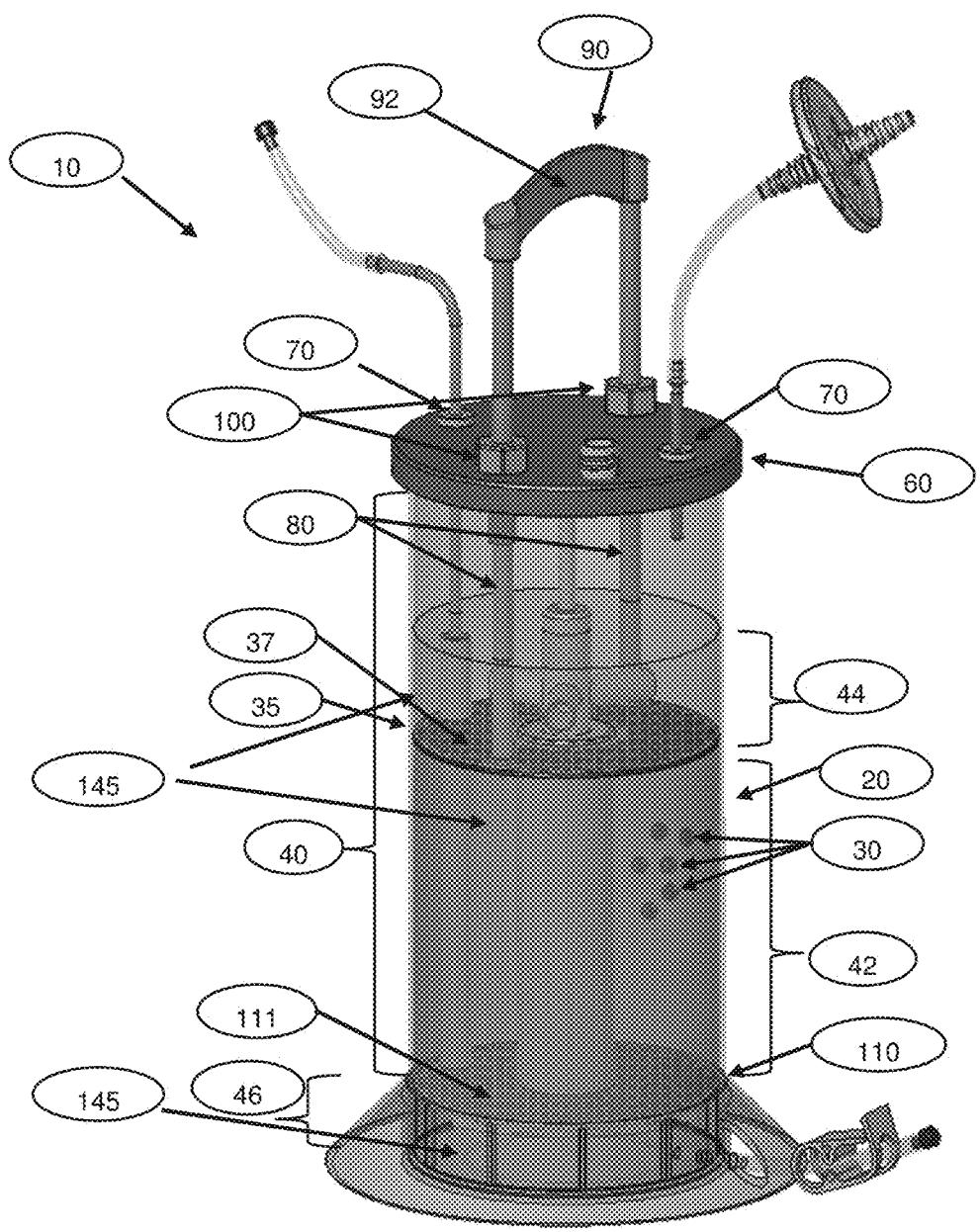
FIG. 1 is a perspective view of a system for growing and harvesting cells, according to an exemplary embodiment.
Figure 2:
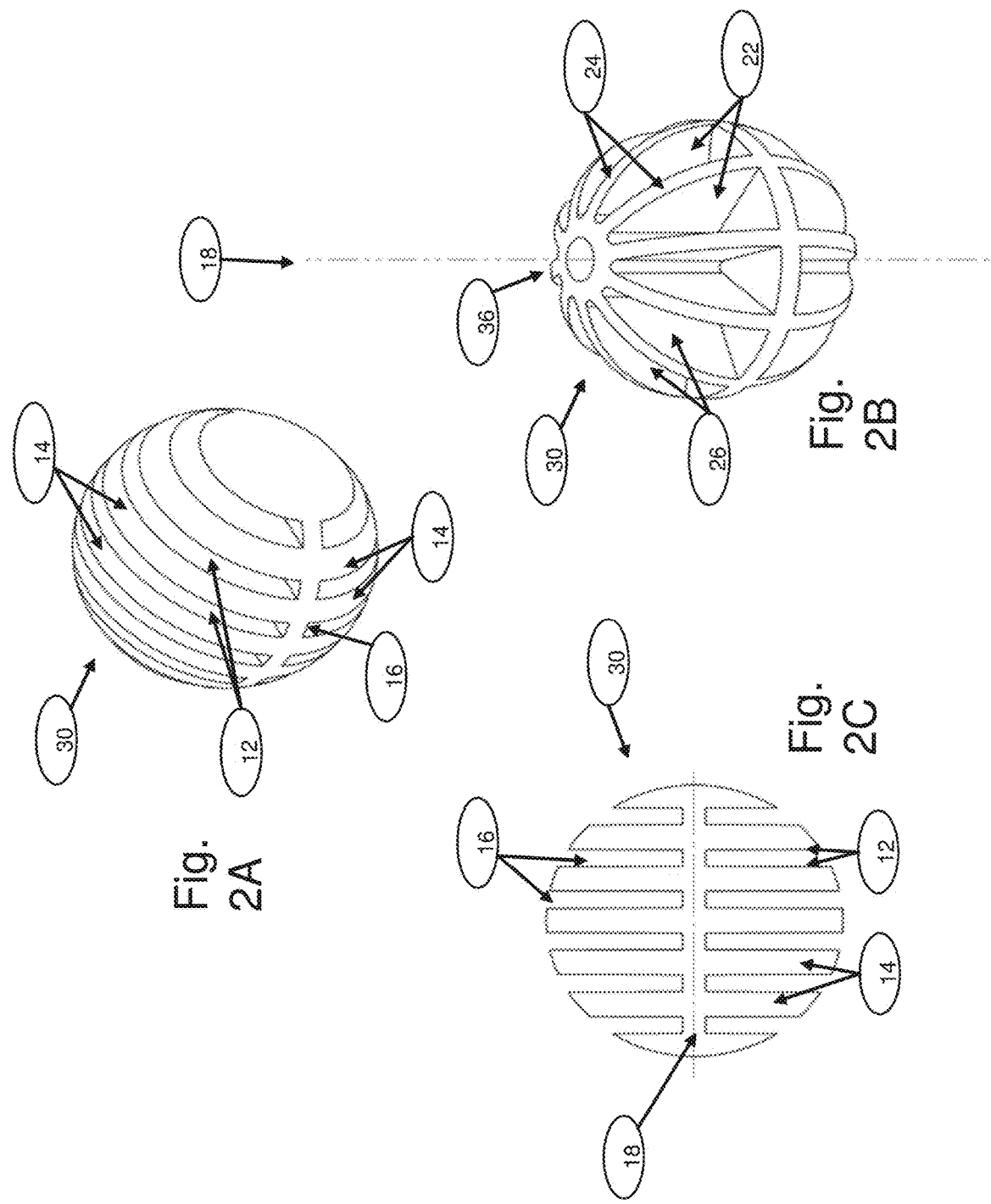
FIG. 2A is a perspective view of a carrier (or "3D body"), according to an exemplary embodiment.
FIG. 2B is a perspective view of a carrier, according to another exemplary embodiment.
FIG. 2C is a cross-sectional view of a carrier, according to an exemplary embodiment.
Figure 3:
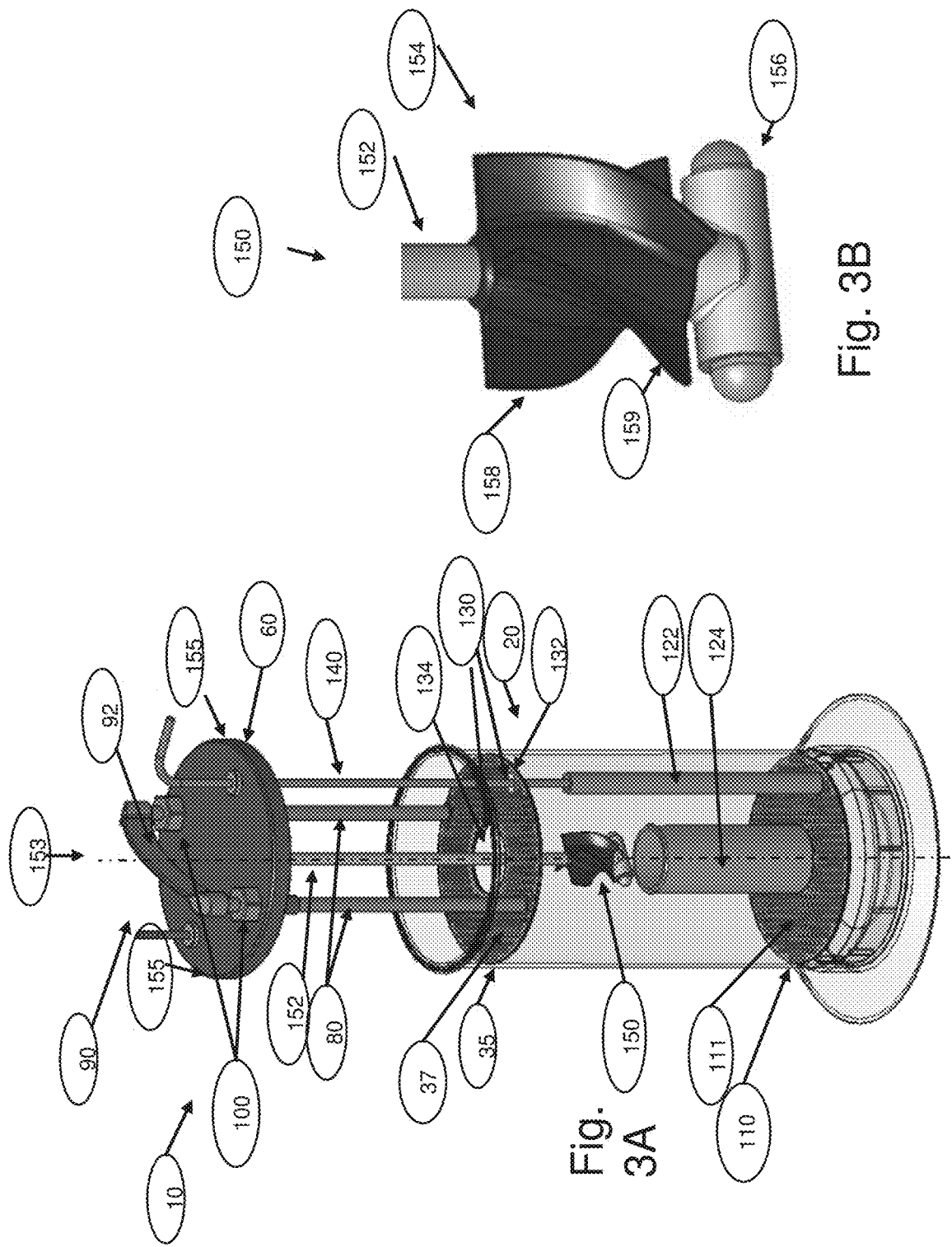
FIG. 3A is a perspective view of a system in an open configuration, according to an exemplary embodiment.
FIG. 3B is a perspective view of an impeller, according to an exemplary embodiment.

Reference will now be made in detail to the present embodiments of the disclosure, examples of which are illustrated in the accompanying drawings.

In this application, the use of the singular includes the plural unless specifically stated otherwise. Also in this application, the use of "or" means "and/or" unless stated otherwise. Furthermore, the use of the term "including," as well as other forms, such as "includes" and "included," are not limiting. Any range described herein will be understood to include the endpoints and all values between the end points.

The systems and devices of the present disclosure are configured for growing and harvesting cells. Certain embodiments of these vessels are configured to operate with various shaped and sized carriers, including but not limited to spherical, cylindrical, cubical, hyperrectangular, ellipsoid, and polyhedral shapes, having a variety of sizes, as specified herein. In some embodiments, these carriers allow growth (proliferation) of eukaryotic cells. "Two dimensional (2D) growth" will be understood to include proliferation of eukaryotic cells on a surface. In some embodiments, expansion of cells results in a substantial monolayer of cells on a surface.

A "majority of cell growth in a monolayer" will be understood to include, in various embodiments, at least 50%, at least 60%, at least 70%, at least 80%, at least 90%, at least 95%, or at least 99% of cells present on a surface in a monolayer, as opposed to multilayered growth. 2D growth can include growth along planar (i.e., flat) surfaces and/or growth along curvilinear surfaces, as described in more detail below. Thus, a "2D surface" will be understood to include a planar or substantially planar surface or a curvilinear surface. In certain embodiments, the 2D surface is a non-porous surface, or, if pores are present, they are no larger than 20 microns, in other embodiments 10 microns, in other embodiments 5 microns, in other embodiments 3 microns, in other embodiments 2 microns, or in other embodiments 1 micron.

In some embodiments, the systems of the present disclosure in some embodiments provide for high surface area to volume (SA:V) ratios, thereby allowing growth of high quantities of cells in low volumes, as compared to traditional growth in flasks. Furthermore, the systems of the present disclosure, in other embodiments, facilitate harvesting of cells after growth and/or transfer of cells to other environments for storage, commercial use (e.g., as therapeutic agents), or for growth of additional cells. Furthermore, the devices and systems described herein can, in other embodiments, be configured to allow high-quality cell growth that is at least as efficient as that achieved using standard cell culture systems in terms of cell viability, attachment, and/or maintenance or control of other cell properties.

In various embodiments, the systems of the present disclosure can be used to culture a variety of different eukaryotic cell types. For example, the systems can be suitable for growth of stem cells, anchorage-dependent cells, mesenchymal cells, and adherent cells. As used herein the phrase "adherent cells" refers to cells that are capable of attaching to an attachment substrate and expanding or proliferating on the substrate. In some embodiments, the cells are anchorage dependent, i.e., require attachment to a surface in order to proliferate grow in vitro. Suitable adherent cells can include adherent stromal cells, which may be a heterogeneous population of cells obtained from, e.g., bone marrow, adipose tissue, placenta, cord blood, and peripheral blood, and which, in various embodiments, may or may not be capable of differentiating into different types of cells (e.g. reticular endothelial cells, fibroblasts, adipocytes, osteogenic precursor cells), depending upon influences from bioactive factors.

Alternatively or in addition, the cells are mesenchymal-like adherent stromal cells (ASC), which exhibit a marker pattern similar to mesenchymal stromal cells, but do not differentiate into osteocytes, under conditions where "classical" mesenchymal stem cells (MSC) would differentiate into osteocytes. In other embodiments, the cells exhibit a marker pattern similar to MSC, but do not differentiate into adipocytes, under conditions where MSC would differentiate into adipocytes. In still other embodiments, the cells exhibit a marker pattern similar to MSC, but do not differentiate into either osteocytes or adipocytes, under conditions where mesenchymal stem cells would differentiate into osteocytes or adipocytes, respectively. The MSC used for comparison in these assays are, in some embodiments, MSC that have been harvested from bone marrow (BM) and cultured under 2D conditions. In other embodiments, the MSC used for comparison have been harvested from bone marrow (BM) and cultured under 2D conditions, followed by 3D conditions. In more particular embodiments, the mesenchymal-like ASC are maternal cells. In alternative embodiments, the mesenchymal-like ASC are fetal cells.

Growth efficiency of various types of adherent cells can be influenced by environment and/or contact with other cells during growth. For example, adherent cells may be brought into contact with other adherent cells. If one monolayer of cells contacts another monolayer of cells, the two monolayers may interact with each other, e.g. via intercellular junctions. Such interaction between cells grown on different carriers may result in attachment of carriers to each other. The interaction may be mediated by extracellular matrix secreted by the cells. Because some embodiments of the systems described herein can limit such unwanted cell-to-cell interactions, e.g. due to their configuration, clumping or aggregation can be generally limited. In addition, certain embodiments of the present systems can provide a stable growth scaffold for cell growth and maintenance. Other embodiments of the systems provide methods for efficient harvesting of cells. Moreover, in still other embodiments, the systems are configured to deliver nutrients, medium, gases, and other fluids to provide a stable environment for growing monolayers of adherent cells. The systems may also promote more consistent growth of cells by limiting growth under 3D conditions as compared to 2D conditions. The phrase "3D growth" refers to growth that allows cell-to-cell contact outside of the plane of a monolayer. In some embodiments, 3D growth is carried out under conditions that include a 3D growth surface, in some embodiments comprising an adherent material, which allows cells to grow in a 3D orientation relative to one another.

In various embodiments, the systems described herein are configured to permit efficient seeding and/or growth of cells on a plurality of carriers, and harvesting of the cells from the carriers. The systems can include a range of sizes from small to large volumes, and can include a range of different embodiments using one or more features described herein. In certain embodiments, the systems include a packed configuration, wherein the plurality of carriers are packed to form a packed bed of carriers. With limited or no movement of the carriers, cells can be seeded, grown, and maintained. A population of cells may be selected by controlling and/or monitoring one or more medium parameters, such as, for example, pH, glucose, and dissolved oxygen (DO) concentration. To harvest the cells, the packed bed of carriers can be unpacked or released, allowing at least some of the carriers to be mixed or to otherwise move. In more specific embodiments, the bioreactor is agitated, for example as described in PCT Publ. No. WO 2012/140519, which is incorporated herein by reference in its entirety. In some embodiments, the agitation is "vibration" as described in WO 2012/140519, the contents of which relating to vibration are incorporated herein by reference. In more specific embodiments, either the basket as a whole can be moved, or the carriers can be mixed inside the basket. Agitating the carriers enhances, in some embodiments, release of cells from the carriers. In some cases, collisions between carriers and other carriers or with a wall or component of the vessel can facilitate release of cells from the carriers, while in other embodiments, for example when the basket is moved through an aqueous medium, it may not be necessary for the carriers to collide with one another in order to dislodge the cells therefrom.

In other aspects, carriers can be used to transport cells. For example, cells can be transported from one growth vessel to another. In more specific embodiments, cells may be seeded on carriers in one type of vessel and then transported while on the carriers to another vessel for growth. Cells may also be seeded on carriers in a growth vessel, removed from the carriers and re-suspended in a medium within the same vessel, and then transported to another vessel for seeding.

Some embodiments of the carriers described in PCT Publication Number WO/2014/037862, published on Mar. 13, 2014, which is incorporated herein by reference in its entirety, and herein are configured to generally limit contact between surfaces to allow cellular growth. As such, carriers can be generally circular, rounded, or arcuate to generally minimize contact between surfaces of adjacent carriers. Individual carriers can be designed to contact adjacent carriers over a relatively small area. Such limited inter-carrier contact can provide growing surfaces that subject growing cells to relatively small interactions with other cells growing on other carriers.

As provided herein, multiple carriers in a single incubation vessel can provide a more efficient, controlled, and stable growth environment for adherent cells. Packing and unpacking these carriers can further provide advantages in seeding, growing, and harvesting cells grown on these carriers. In certain embodiments, the step of packing includes moving a component of the vessel to a first position, wherein, in more specific embodiments, the component is a solid structure that defines a wall of the compartment wherein the carriers are located. Alternatively or in addition, the first position of the component compresses the carriers. The step of packing includes, in other embodiments, moving the component to a second position. In certain embodiments, the second position decompresses the carriers, and/or is further away from the center of the compartment. For example, in the case of a movable upper component that defines the ceiling of the compartment wherein the carriers are located, the first position would be downward relative to the second position.

The methods of cell growth and/or harvesting described herein may also be configured for use with the systems described herein. In certain embodiments, vessels configured to generally resist cellular attachment are used with these carriers. For example, vessels formed from or coated with glass or plastics known to limit cellular adhesion can be used. Such vessels can encourage suitable growth of monolayers of adherent cells on the carriers described herein. Such vessels may also limit possible unwanted cellular interactions, which may result in inadvertent cell-to-cell adhesions as described herein.

Certain embodiments of methods described herein are suitable for small-scale laboratory production. In other embodiments, methods described herein are suitable for large-scale commercial or industrial production. One of ordinary skill will appreciate that aspects of the systems and methods described herein could be used for either small-scale or large-scale growth and/or harvesting of cells.

According to various embodiments, systems and methods for cell-culture are provided. The systems can comprise a vessel configured to receive carriers comprising multiple 2D surfaces, wherein these multiple 2D surfaces are configured to support monolayer growth of eukaryotic cells over at least a majority of the 2D surfaces.

The vessel can also include a component configured to pack the carriers to form a packed bed. As described below, the component can form part of a basket configured to contact some of the packed carriers to limit their movement. With limited movement, the carriers can provide stable 2D surfaces for cell growth. Once grown, the cells can then be harvested by unpacking the carriers. Moving carriers can collide with other carriers, or the vessel, to facilitate release of the cells from the 2D surfaces of the carriers. Various systems and methods for agitating carriers to release cells are described herein.

The systems of the present disclosure can be sized and configured to facilitate cell growth and harvesting. FIGS. 1-5B illustrate systems configured generally for large-scale cell growth, which are described in more detail below. In addition, FIGS. 6-7B illustrate systems configured generally for small-scale cell growth. It will be appreciated that the systems and methods shown in the figures and described below are exemplary, and that various features from the different embodiments described herein may be combined or interchanged.

FIG. 1 is a perspective view of a system 10 for cell growth and harvesting, according to certain embodiments. Although system 10 is ordinarily kept closed, it is generally depicted opened in the Figures herein in order to show the inner components. As shown, system 10 includes a vessel 20 configured to receive a plurality of carriers 30 (see FIGS. 2A-B and description below), which may be located within a chamber 40 of vessel 20. For simplicity, only 3 carriers are shown; a much larger number will typically be present.

System 10 can also include a component 35, which serves to confine carriers by preventing them from moving further towards upper plate 60. In certain embodiments, component 35 is configured to allow packing and unpacking of carriers 30 within vessel 20. As shown in FIGS. 1 and 3A, component 35 may be located inside said chamber 40 of vessel 20. Component 35 may separate chamber 40 into one or more regions. For example, component 35 may separate chamber 40 into a middle region 42 and a second region 44. In operation, middle region 42 may be filled with carriers 30 (not shown). Component 35 may then be moved to apply a compressive force to carriers 30 to pack them into a specific volume of middle region 42. In this packed configuration, carriers 30 may remain stationary within middle region 42. Medium 145 in second region 44 may be stirred and may move through middle region 42, allowing growth of cells on carriers 30 contained within middle region 42. In addition, chamber 40 may include a third region 46. Second and third regions 44, 46 may be located on two or more sides of middle region 42 to provide buffer regions where medium 145 may be stirred to provide flow of medium 145 across carriers 30 located within middle region 42. Accordingly, component 35 (also referred to as the "second perforated structure") may be porous and may have upper pores 37 of sufficient size to permit flow of medium 145 across component 35, yet retain carriers within middle region 42. Component 35 could be formed of any suitable material, such as, for example, a polymer, a metal alloy, or a combination of various materials. In certain embodiments, component 35 may be configured to provide a plunger-like action whereby movement of component 35 compresses carriers 30 located within chamber 40. In other embodiments, middle region 42 may be subdivided into multiple compartments by adding one or more additional component 35 (not depicted)

In some embodiments, component 35 may be moveably coupled to vessel 20. As shown in FIGS. 1 and 3A, component 35 may be moved vertically relative to vessel 20. In other embodiments, component 35 may be moved horizontally, may expand or contract, or may be moved in some other way to restrict the movement of carriers 30 within vessel 20.

As shown in FIGS. 1 and 3A, system 10 can include an upper cover or plate 60 configured to couple to vessel 20. In some embodiments, upper cover or plate 60 can be configured to seal chamber 40, which is configured to receive a range of carriers. Upper cover or plate 60 can also include one or more ports 70. System 10 can include tubing, sensors, mechanical members, impeller shafts and other devices requiring access to chamber 40.

For example, upper plate 60 can include one or more ports 70 configured to receive one or more support members 80 coupled to component 35. Ports 70 are preferably sealed such as to prevent introduction of bacteria or other biological contaminants. As illustrated in the embodiments shown in FIGS. 1 and 3A, two support members 80 can be fixedly coupled to component 35, and may extend upwards from component 35 and through two ports 70 of upper cover or plate 60. And while shown as separate, component 35 and support members 80 could be formed as a single-piece or monolithic device. Component 35 and support members 80 could be formed from plastic, metal, glass, or other suitable material.

Component 35 and/or support members 80 could also be coupled to a handle 90. Handle 90 can include a grip 92 configured to allow an operator to move component 35 from a first position to a second position as described above. As shown in FIG. 1, handle 90 may be used to raise and lower component 35 to pack and unpack carriers 30.

System 10 can also include one or more locking elements 100 configured to lock component 35 in one or more positions. For example, locking element 100 could lock component 35 in at least one of the first position and the second position relative to vessel 20. Locking element 100 is depicted as a bolt, but could include any similar device that engages upper plate 60 and/or support member 80. The mechanism could for example utilize a thread (not visible). Locking element 100 could also include a latch, cleat, friction fit, button, gear, motor, or other device (not depicted) configured to lock component 35, support member 80, and/or handle 90 in one or more positions relative to vessel 20.

System 10 may also include a lower component 110 configured to support carriers within vessel 20. As shown in FIGS. 1 and 3A, lower component 110 can be located at a distance from a lower surface of vessel 20. In particular, lower component 110 can be shaped and sized for locating within chamber 40 such that third region 46 includes a volume of medium 145. Similar to component 35 described above, lower component 110 (also referred to as the "first perforated structure") can be porous with lower pores 111 of sufficient size to permit flow of medium 145 between middle region 42 and third region 46 while maintaining carriers within middle region 42. In certain embodiments, carriers 30 are located in middle region 42 between component 35 and lower component 110.

In some embodiments, component 35 and/or lower component 110 may also include one or more apertures 130 configured to receive one or more conduits 122,124. As shown in FIG. 3A, multiple conduits 122,124 can extend generally between component 35 and lower component 110 via apertures 130. Conduits 122,124 can provide direct fluid passage between second region 44 and third region 46. For example, a first conduit 122 and a second conduit 124 can extend upwards from lower member 110 towards component 35. Component 35 may include one or more apertures 130 sized and located to receive associated conduits 122,124. In particular, component 35 can include a first aperture 132 associated with first conduit 122 and a second aperture 134 associated with second conduit 124. As shown in FIG. 3A, first conduit 122 and first aperture 132 can be located, shaped, and sized to receive a line 140. Line 140 may provide a direct passageway for transport of fluid to or from third region 46 and through upper plate 60.

As shown in FIG. 3A, shaft 152, second conduit 124, and second aperture 134 may be located on a central longitudinal axis 153 of vessel 20. Line 140, first conduit 122, and first aperture 132 may be located about a periphery 155 of chamber 40, off the central longitudinal axis 153 of vessel 20.

Figure 4:
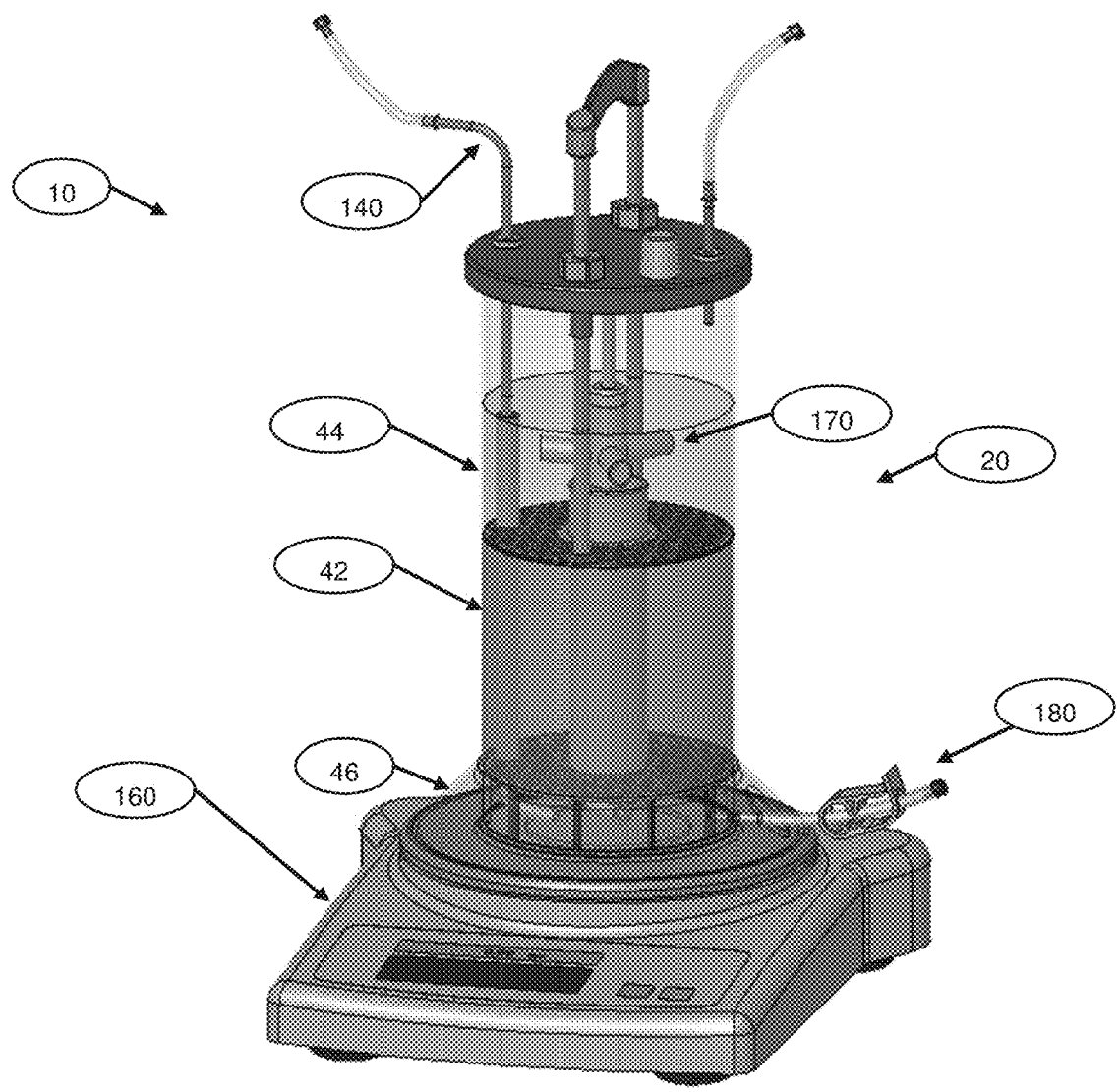
FIG. 4 is a perspective view of a system for growing and harvesting cells in an opened position, according to another exemplary embodiment.

Second conduit 124 and second aperture 134 may also be located, shaped, and sized to receive a bladed impeller 150. As shown in FIGS. 3A-B, bladed impeller 150 can include a shaft 152 optionally coupled to upper plate 60, a blade 154 configured to move fluid when rotated, and/or a magnetic element 156 configured to magnetically couple to a stirring device 160 (FIG. 4). In certain embodiments (FIG. 3B), bladed impeller 150 comprises 2-5 blades 154 that extend substantially radially from shaft 152 throughout their length. The plane of the distal end 158 of the blade 154 relative to magnetic element 156 is substantially parallel to the axis (90 degrees [deg.] slope relative to magnetic element 156), and the slope of the plane gradually decreases from 90 degrees (deg.) to reach between 30-60 deg. at the proximal end 159 of the blade 154 relative to magnetic element 156. In certain embodiments, bladed impeller 150 may rotate to move medium 145 through middle region 42 and over cells growing on carriers 30. Shaft 152 can be fixedly coupled to upper plate 60 and rotationally coupled to blade 154 and/or magnetic element 156. Alternatively, shaft 152 can be fixedly coupled to blade 154, magnetic element 156, and/or cell-lift impeller 170 (see FIG. 17A) and/or can be rotationally coupled to upper plate 60. In other embodiments, shaft 152 could be coupled to a motor (not shown) or other device configured to rotate shaft 52 and blade 154. Such an embodiment would not require magnetic element 156.

It is contemplated that various features described above may be provided on different devices and that different configurations of devices are possible. For example, conduits 122,124 may be coupled to component 35, upper plate 60, or another part of system 10. Likewise apertures may be provided in lower component 110, vessel 20, or another part of system 10. In some embodiments, an upper impeller 170 may be provided in second region 44 of chamber 40 to aid circulation of medium 145 throughout chamber 40. Additional probes, lines, and other devices (not depicted) may be provided within chamber 40 and different regions 42, 44, and 46. Accordingly, component 35 and lower component 110 may be configured to operate with these additional devices.

As described herein, with reference to FIGS. 2A-B, and in WO/2014/037862, published on Mar. 13, 2014, which is incorporated herein by reference in its entirety, carriers 30 can include multiple 2D surfaces 12 extending from an exterior of carrier 30 towards an interior of carrier 30. As shown, the surfaces are formed by a group of ribs 14 that are spaced apart to form openings 16, which may be sized to allow flow of cells and culture medium (not shown) during use. With reference to FIG. 2C, carrier 30 can also include multiple 2D surfaces 12 extending from a central carrier axis 18 of carrier 30 and extending generally perpendicular to ribs 14 that are spaced apart to form openings 16, creating multiple 2D surfaces 12. In some embodiments, carriers 30 are "3D bodies" as described in WO/2014/037862; the contents of which relating to 3D bodies are incorporated herein by reference.

As mentioned, carrier 30 may have a variety of shapes, including but not limited to spherical, cylindrical, cubical, hyperrectangular, ellipsoid, and polyhedral and/or irregular polyhedral shapes. In some embodiments, the diameter of the minimal bounding sphere (e.g. the diameter of the carrier, in the case of a spherical shape) of carrier 30 can range from 1-50 mm. In other embodiments, the outer largest dimension can range from 2-20 mm, from 3-15 mm, or from 4-10 mm. In other embodiments, the generic chord length of carriers 30 ranges from 0.5-25 mm, from 1-10 mm, from 1.5-7.5 mm, from 2-5 mm, or from 2.5-4 mm. As known to those skilled in the art, generic chord length is described inter alia in Li et al, Determination of non-spherical particle size distribution from chord length measurements. Part 1: Theoretical analysis. Chemical Engineering Science 60(12): 3251-3265, 2005)

Depending upon the overall size of carrier 30, ribs 14 and openings 16 can be variously sized. For example, ribs 14 can range in thickness from 0.1-2 mm or from 0.2 mm-1 mm. In particular, ribs 14 can be 0.4-0.6 mm, 0.5-0.7 mm, or 0.6-0.8 mm in thickness. Openings 16 can range in width from 0.01-1 mm or from 0.1-0.5 mm. In particular, openings 16 can be 0.25-0.35 mm, 0.35-0.45 mm, or 0.45-0.55 mm in width.

In preferred embodiments, the carriers provide 2D surfaces for attachment and monolayer growth over at least a majority of or all of the surface area of the multiple 2D surfaces 12, 22. Alternatively or in addition, the carriers have a surface area to volume ratio is between 3-1000 $cm^2/cm^3$, between 3-500 $cm^2/cm^3$, between 3-300 $cm^2/cm^3$, between 3-200 $cm^2/cm^3$, between 3-100 $cm^2/cm^3$, between 3-50 $cm^2/cm^3$, between 3-30 $cm^2/cm^3$, between 5-20 $cm^2/cm^3$, or between 10-15 $cm^2/cm^3$.

As shown in FIGS. 2A-B, carriers 30 may be substantially spherical and have a diameter that forms the carriers' largest dimension. In some embodiments, a diameter of carrier 30 can range from 1-50 mm. In other embodiments, the diameter can range from 2-20 mm, 3-15, mm, or 4-10 mm. Depending upon the overall size of carrier 30, ribs 24 and openings 26 can be variously sized. For example, ribs 24 can range in thickness from 0.1-2 mm or from 0.2-1 mm. In particular, ribs 24 can be 0.45-0.55 mm, 0.55-0.65 mm, or 0.65-0.75 mm in thickness. As shown in FIG. 2B, a minimum width of openings 26 can range from 0.01-1 mm, from 0.05-0.8 mm, or from 0.1-0.5 mm. Specifically, the minimum width of openings 26 can be 0.25-0.35 mm, 0.3.5-0.45 mm, or 0.45-0.55 mm. In other embodiments, the largest cross-sectional dimension of opening 36 can range from 0.1-5 mm, from 0.2-3 mm, or from 0.5-2 mm. More particularly, opening 36 can have a largest cross-sectional dimension of 0.7.5-0.85 mm, 0.95-1.05 mm, or 1.15-0.25 mm.

In the embodiment shown in FIG. 2A, ribs 14 are substantially flat and extend parallel to one another. In other embodiments, the ribs are in other configurations. For example, FIG. 2B illustrates carrier 30 having multiple two-dimensional surfaces 22 formed by ribs 24 in a different configuration. In particular, ribs 24 are shaped to form openings 26 that are spaced around the circumference of carrier 30, whereby openings 26 can be generally wedge shaped. Ribs 24 can extend generally radially from a central carrier axis 18 of carrier 30 to a peripheral surface of carrier 30. Carrier 30 can also include one or more lateral planes extending from the central carrier axis 18 of carrier 30 and extending generally perpendicular to ribs 24, as depicted in FIG. 2C, which is a cross-sectional view of certain embodiments of the carrier 30 of FIG. 2A. Further, carrier 30 includes an opening 36 extending through the carrier's center and forming additional surfaces 32, which can support monolayer growth of eukaryotic cells.

In still other embodiments, the material forming the multiple 2D surfaces comprises at least one polymer. In more specific embodiments, the polymer is selected from a polyamide, a polycarbonate, a polysulfone, a polyester, a polyacetal, and polyvinyl chloride.

The material used to produce the described carriers can include, in various embodiments, metals (e.g. titanium), metal oxides (e.g., titanium oxide films), glass, borosilicate, carbon fibers, ceramics, biodegradable materials (e.g. collagen, gelatin, PEG, hydrogels), and or polymers. Suitable polymers may include polyamides, such as GRILAMID® TR 55 (EMS-Grivory, Sumter, S.C.); polycarbonates such as LEXAN® (Sabic, Pittsfield, Mass.) and Macrolon® (Bayer); polysulfones such as RADEL® PPSU (Solvay) and UDEL® PSU (Solvay); polyesters such as TRITAN® (Polyone) and PBT® HX312C; polyacetals such as CELON® (Ticana), and polyvinyl chloride. In certain embodiments, the described carriers are composed of a non-porous material, or, if pores are present, they are no larger than 20 microns, in other embodiments 10 microns, in other embodiments 5 microns, in other embodiments 3 microns, in other embodiments 2 microns, or in other embodiments 1 micron.

In more specific embodiments, cell-culture carriers are formed of injection-molded surface treatment of LEXAN® or GRILAMID®, with a smooth surface texture, using growth medium proteins and/or polylysine on LEXAN® or GRILAMID® carriers; cell-culture carriers formed of injection-molded GRILAMID® with a rough surface that was preincubated with growth medium proteins. In other embodiments, untreated LEXAN® or GRILAMID® surfaces are utilized.

In other embodiments, at least part of the carriers may be formed using a polystyrene polymer. The polystyrene may be further modified using corona discharge, gas-plasma (roller bottles and culture tubes), or other similar processes. These processes can generate highly energetic oxygen ions which graft onto the surface polystyrene chains so that the surface becomes hydrophilic and negatively charged when medium is added. Furthermore, any of the carriers may be produced at least in part from combinations of materials. Materials of the carriers can be further coated or treated to support cell attachment. Such coating and/or pretreatment may include use of collagen I, collagen IV, gelatin, poly-d-lysine, fibronectin, laminin, amine, and carboxyl.

In various embodiments, the described carriers are coated with one or more coatings. Suitable coatings may, in some embodiments, be selected to control cell attachment or parameters of cell biology. Suitable coatings may include, for example, peptides, proteins, carbohydrates, nucleic acid, lipids, polysaccharides, glycosaminoglycans, proteoglycans, hormones, extracellular matrix molecules, cell adhesion molecules, natural polymers, enzymes, antibodies, antigens, polynucleotides, growth factors, synthetic polymers, polylysine, drugs and/or other molecules or combinations or fragments of these.

Furthermore, in various embodiments, the surfaces of the carriers described herein may be treated or otherwise altered to control cell attachment and or other biologic properties. Options for treating the surfaces including chemical treatment, plasma treatment, and/or corona treatment. Further, in various embodiments, the materials may be treated to introduce functional groups into or onto the material, including groups containing hydrocarbons, oxygen, and/or nitrogen. In addition, in various embodiments, the material may be produced or altered to have a texture to facilitate settling of cells or control other cell properties. For example, in some embodiments, the materials used to produce the cell-culture carriers have a roughness on a nanometer or micrometer scale that facilitates settling of cells and/or controls other cell properties.

Other examples of possible alternate embodiments include providing one or more impellers 150 within one or more regions 42, 44, 46 of chamber 40. A lower line 180 may (FIG. 4) or may not (FIG. 3A) be fluidly coupled directly to third region 46 through a wall of vessel 20. And in some embodiments, system 10 may not require lower component 110 or third region 46. Sufficient flow of medium 145 may be achieved using lines suitably positioned about the lower part of chamber 40. For example, additional lines (not shown) may extend down from upper plate 60 about a periphery 155 of chamber 40 with openings into middle region 42. Single or multiple inlet and/or outlet lines 140 and/or conduits 122,124, containing one or more openings, could provide middle region 42 with sufficient flow of medium 145 to provide adequate incubation conditions. In other embodiments, conduit 124 may be removed and/or a suitably configured impeller, for example a bladed impeller 150, may be used to move medium 145 through middle region 42. In yet another embodiment, a packed bed of carriers 30 may be moved as a single entity within the medium 145.

As shown in FIG. 4 and described above, system 10 can include stirring device 160. Stirring device 160 can be set manually or programmed to automatically specific rates of rotation to one or more impellers 150, 170. System 10 can also include a station 190 (FIG. 5A) configured for industrial scale production. Station 190 can include one or more processors 195 and user interface 196 configured to monitor and/or control aspects of system 10. For example, station 190 could be configured to monitor and/or control pH, DO, temperature, impeller speed, or other parameter(s) associated with system 10.

Figure 5B:
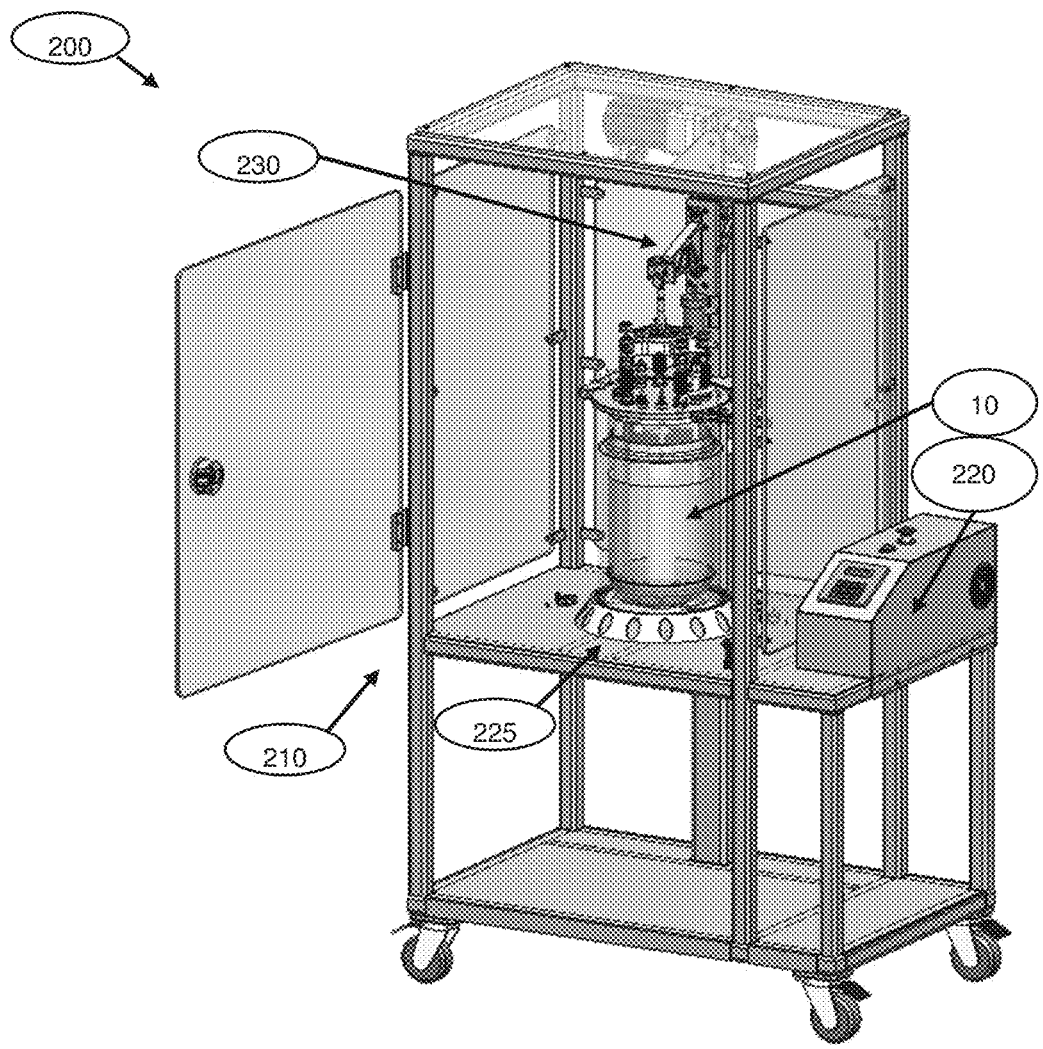
FIG. 5B is a perspective view of a system under harvesting conditions, according to an exemplary embodiment.

FIG. 5B shows a harvest device 200, according to an exemplary embodiment. Harvest device 200 can be configured to couple to system 10 to agitate (or vibrate) carriers 30. For example, harvest device 200 could include an enclosure 210 configured to receive system 10. Once located within enclosure 210, system 10 or chamber 40 thereof may be agitated to facilitate detachment of cells from carriers 30. Harvest device 200 can include an agitation (or vibration) device 220 configured to control and/or apply agitation to system 10. For example, agitation device 220 can include a base or other receptacle 225 configured to receive vessel 20. Once locked within enclosure 210, agitation device 220 could apply a force to vessel 20 to agitate carriers 30 within chamber 40, in some embodiments in the presence of medium (not depicted). In certain embodiments, support member 80 is operably connected to chamber 40, for example via attachment to component 35), thereby enabling agitation of chamber 40 by application of force outside of vessel 20 without exposing the contents of vessel to outside contamination.

Harvest device 200 could also include an actuator 230 configured to control movement of component 35. For example, actuator 230 may couple to handle 90, support member 80, or component 35. Coupling could be releasable. Once coupled, actuator 230 may provide sufficient force to component 35 to move component 35 from the first position to the second position, or in other embodiments to impart a repeated oscillating motion to component 35. Movement and/or positioning of component 35 may be correlated with agitation of carriers 30. For example, actuator 230 may move component 35 to provide greater than about 5%, about 10%, about 25%, or about 50% headspace 50 (see FIG. 13C). Once suitable headspace 50 is created in middle region 42, agitation device 220 may supply sufficient agitation to carriers 30 to facilitate detachment of cells from carriers 30. Such agitation may also be coordinated with the addition of a factor to chamber 40, wherein the factor may also facilitate detachment. The factor could include an enzyme, such as, for example, TrypLE™, optionally also comprising a calcium chelator. Non-limiting examples of a protease plus a calcium chelator are trypsin, or another enzyme with similar activity, optionally in combination with another enzyme, non-limiting examples of which are Collagenase Types I, II, III, and IV, with EDTA. Enzymes with similar activity to trypsin are well known in the art; non-limiting examples are TrypLE™, a fungal trypsin-like protease, and Collagenase, Types I, II, III, and IV, which are available commercially from Life Technologies. Enzymes with similar activity to collagenase are well known in the art; non-limiting examples are Dispase I and Dispase II, which are available commercially from Sigma-Aldrich.

In still other embodiments, harvest device 200 is configured to effect oscillating agitation as described in PCT International Application Publ. No. WO 2012/140519. In certain embodiments, during harvesting, chamber 40 is agitated at 0.7-6 Hertz, or in other embodiments 1-3 Hertz. In certain embodiments, chamber 40 is configured to effect agitation at 0.7-6 Hertz, or in other embodiments 1-3 Hertz, while submerged in a solution or medium. In certain embodiments, support member 80 is operably connected to chamber 40, for example via attachment to component 35), thereby enabling oscillating agitation of chamber 40 by application of force outside of vessel 20 without exposing the contents of vessel to outside contamination.

In other embodiments, harvest device 200 may not require agitation device 220. Instead, actuator 230 could be programmed to move with sufficient speed to agitate carriers 30 to cause collisions to detach the cells.

Figure 8:
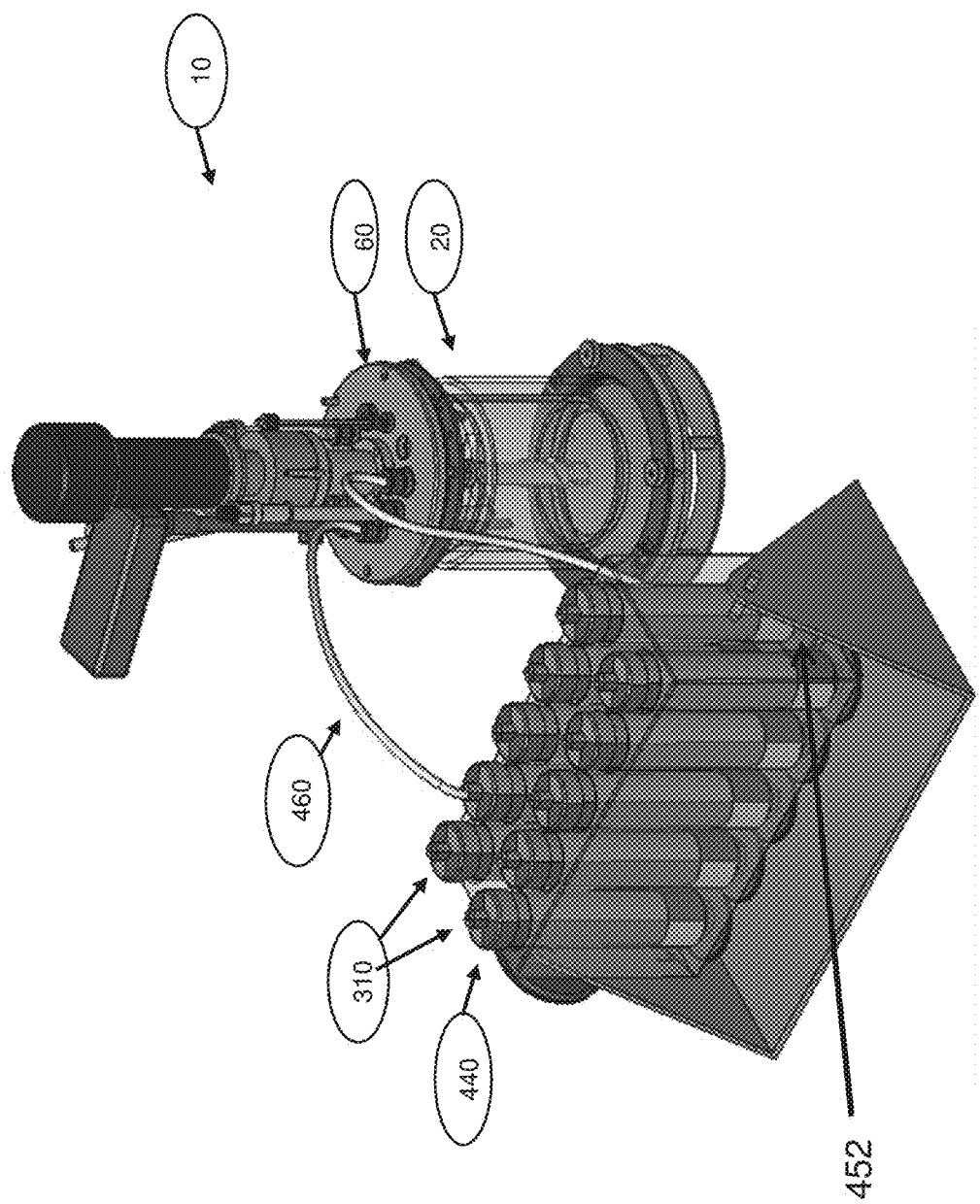
FIG. 8 is a perspective view of two connected systems for growing and harvesting cells, according to an exemplary embodiment.

The systems, devices, and methods described above are generally configured for large-scale industrial application, where cells in volumes from 1 to 100 liters are typically grown and harvested. The embodiments described below and shown in FIG. 6-7B are generally configured for small-scale laboratory application, typically involving cells grown and harvested in less than about 1 liter of medium. However, as shown in FIG. 8, aspects of both small-scale and large-scale systems can be combined.

FIG. 6 illustrates a small-scale system 310, according to another exemplary embodiment. As shown, small-scale system 310 can include a vessel 320 having chamber 340. Within chamber 340, small-scale system 310 can include an upper component 335 configured to pack carriers 30 (not shown), as described above. Specifically, upper component 335 may be configured to move to pack carriers 30 within a first region 342. A second region 344 above upper component 335 may be provided in chamber 340 when upper component 335 is in a first position and carriers 30 are packed. Upper component 335 may also be moved to a second position when carriers 30 are unpacked. As shown in FIG. 6, with upper component 335 in the second position, carriers 30 within first region 342 may move and collide with each other or vessel 320. When upper component 335 is in the first position, carriers within first region 342 may be generally stationary.

As shown in FIG. 6, first region 342 may be bounded above by upper component 335 and below by a lower component 410. Lower component 410 may separate first region 342 from a third region 346. Lower component 410 may be fixedly located within vessel 320. In some embodiments, lower component 410 may not be required as vessel 320 may be configured to retain carriers within chamber 340. Moreover, chamber 340 may be shaped and sized to receive a relatively small number of carriers 30 (not depicted), such as two, five, ten, twenty, fifty, one hundred, or several hundred carriers 30.

Component 335 may be coupled to a handle 390 via a support member 380. Small-scale system 310 may also include an upper plate 360 having a port 70 configured to receive support member 380. Upper plate 360 may also include a locking element 400 configured to lock component 335 in at least one of the first position (packed bed) and the second position (unpacked bed).

Upper lid or plate 360 may include a seal 420 configured to generally seal vessel 320. Upper lid or plate 360 may also include one or more attachment members 430 configured to attach upper lid or plate 360 to vessel 320. Attachment members 430 can include snap fit, luer lock, threads, or another type of attachment mechanism. One or more surfaces of vessel 320 and upper plate 360 may be configured to engage via a releasable or a non-releasable coupling.

The general structure, function, and equivalents described above for related features of system 10 can be similar to those described above for system small-scale 310. In addition, small-scale system 310 may include a cap (not shown) configured to seal third region 346 when necessary. Moreover, small-scale system 310 may be shaped and sized for placement within standard tubes, such as, for example, Eppendorf tubes, or 50 ml screw cap tubes.

FIGS. 7A and 7B illustrate, respectively, agitation devices that may be used with small-scale system 310. For example, FIG. 7A shows a rolling device 440 configured to rotate one or more small-scale systems 310. As shown, each small-scale system 310 may be associated with a gear 445 configured to rotate. Pulleys, motors, or other devices (not depicted) may also be used to rotate one or more small-scale systems 310. FIG. 7B shows an agitation device 450 that includes a housing 455 configured to receive one or more small-scale vessels 320. Agitation device 450 could apply agitation to housing 455 to agitate cells contained within vessel 320.

FIG. 8 illustrates an embodiment in which one or more small-scale systems 310 are coupled to a system 10. Typically, small-scale systems 310 house carriers 30 (not depicted), and system 10 serves as a fluid reservoir. Rolling device 440 containing small-scale systems 310 is fluidly coupled to system 10 or to a second fluid reservoir 452 within rolling device 440. One or more lines 460 may be used to fluidly couple one or more, or in other embodiments all, of small-scale systems 310 to system 10, typically with a separate line 460 for each small-scale system 310. As shown in FIG. 8, two lines 460 extend from rolling device 440 to upper plate 60 and into chamber 20 of small-scale system 10.

In rolling device 440, each small-scale system 310 may spin around a vertical axis as depicted, in some embodiments independently of one another, or in other embodiments around a horizontal or oblique axis (FIG. 7A). In certain embodiments, the rolling motion is only performed during seeding and over the next few hours.

In another embodiment, the system can include a reservoir vessel. The reservoir vessel can include various types and sizes. For example, reservoir vessel can include a 5 L glass laboratory bottle filled with 1.3 L growth medium. In another example, reservoir vessel can include a New-Brunswick 2.2 L Bioreactor filled with 1.3 L growth medium.

Reservoir vessel can include one or more ports. For example, a first port may be configured to input a fluid (such as medium) into the vessel. A second port may be configured to output a fluid from the vessel. Such ports can provide for circulation of a fluid medium within the biomass vessel (see description of FIG. 15).

As described above, cells can be grown and harvested using one or more systems 10 and/or 310. Several examples of cell growth and harvesting are provided in the following Examples. For each example, cells may be grown on carriers 30 as shown in FIGS. 2A-C or other suitable carriers.

Cells may be grown on carriers 30 located in a suitable cell growth vessel, such as, for example, a bottle or a bioreactor vessel. The bottle may include a 250 ml laboratory bottle and the bioreactor may include a 2.2 l New-Brunswick packed-bed bioreactor.

The bottle growth system may include a combination of two or more vessels. For example, a biomass vessel may include a 250 mL bottle with about 1,300 packed carriers. Such a system may provide a total surface area of about 4,500 cm$^2$. With reference to FIG. 15A, vessel 20 may include one or more ports 70. For example, vessel 20 may include three ports (not depicted). An input tube 580 may be configured to provide input to vessel 20. One port 70 may be configured to receive a fluid, such as a liquid or a gas, and may include medium, oxygen, or other fluids. Port 70 may also include a drip-tube. An output tube 580 may be configured to provide output from the vessel. An additional port 70 may be configured to receive a fluid, such as a liquid or a gas, and may include medium, $CO_2$, or other types of fluids. A third port (not depicted) may be configured to receive or actuate a component configured to pack or unpack carriers (not depicted).

Carriers may be packed or unpacked, in part, using a gas, a liquid, or via a mechanical action. Mechanical action can include agitating the vessel using agitation or vibration, in some cases in the presence of a releasing agent such as a protease. Carriers may be moved to contact each other, the vessel, or another element to provide an impact force on the carriers. Such an impact force may assist release of cells from the carriers.

Fluids can be pumped into or out of a vessel using any suitable device or system. For example, a peristaltic pump (Gilson or Watson Marlow), gravity feed, centrifugal, vacuum, positive displacement, or other type of device can be used to pump a fluid into a vessel or extract a fluid from a vessel.

Vessel may also include another port for gassing. Other ports may be required for control elements, input, output, monitoring, etc.

Cells can then be harvested by different methods and equipment. For example, vortex tapping, silicon sheets tapping, rubber sheets taping and spacing+inverting can be used.

In one embodiment, cells were seeded at 3,000 cells/cm$^2$ density. Initially the cells were suspended in full DMEM growth medium, namely DMEM (Gibco, cat. no. 041-96417A), 10% FBS (Biochrom GmbH, Berlin, Germany; cat. no. S 0115), 20 mM L-Glutamine (Sigma-Aldrich, cat. no. G7513) and 50 micrograms per milliliter (mcg/ml) Gentamicine (HyClone, Fisher Scientific, cat. no. SV30080.10). Cell attachment was achieved by rolling the bottle at 0.1-0.5 RPM on roller instrument for 20 hours. Cells were grown in full DMEM medium with circulation between the biomass vessel and the reservoir vessel for another 3 days (total of 4 days). Cells were then harvested using TrypLE.

During one or more steps described herein, the carriers could be washed with PBS (Gibco, cat. no. 14190-094). Harvesting may include adding one or more factors to the vessel. A factor can include any compound configured to release or aid release of a cell from a carrier. For example, a factor can include an enzyme. In some instances, the factor can include TrypLE (Gibco, cat. no. 12563-029). Harvesting can include incubation with TrypLE at about 37° C. for about 6 minutes.

Following incubation, cells may be separated from growth medium. For example, the cell-containing medium may be centrifuged to separate the cells from the medium. A centrifuge step can include centrifuging at about 300×g for about 10 min. Following centrifugation, cells may be re-suspended. In addition, cells can be counted, for example, with a Casy counter.

Using a bioreactor system, cells may be grown on about 2,000 packed carriers with total surface area of about 7,300 $cm^2$. Cells can be seeded at about 3,000 cells/$cm^2$ density in growth medium (e.g. DMEM), which may be full medium or serum-free medium. Cell attachment may be achieved by applying a stirring speed of 75 RPM or less, preferably 50 RPM or less for about 20 hours. Subsequently, cells can be grown for 2-10 days, in other embodiments 2-8 days, in other embodiments, 2-7 days, in more specific embodiments 2-6 days, in more specific embodiments 3-5 days, in more specific embodiments 3-4 days. Growth can be conducted under various conditions. For example, growth conditions can include generally maintaining medium at about 37° C., DO about 70% air, and pH of about 7.4. Stirring velocity during seeding and over the next few hours may be about 50 RPM, after which, in some embodiments, stirred may be halted or continued only intermittently, or in other embodiments, the stirring speed may be varied, for example decreased, such as 10-40 RPM, or increased, such as 60-150 RPM.

Cells can be harvested by transferring the carriers to a sterile 1 L plastic bottle, then washing the carriers (e.g. with PBS) as described above. The cells may be incubated with about 300 ml TrypLE for about 4-6 min, while typically maintained at room temperature or warmer, e.g. at about 37° C. The bottle may be mixed, e.g. by inverting about 10-20 times. The cell suspension may then be centrifuged, e.g. at about 300×g for about 10 min. Subsequently, the cells may be re-suspended and counted, e.g. using a Casy counter.

Figure 9:
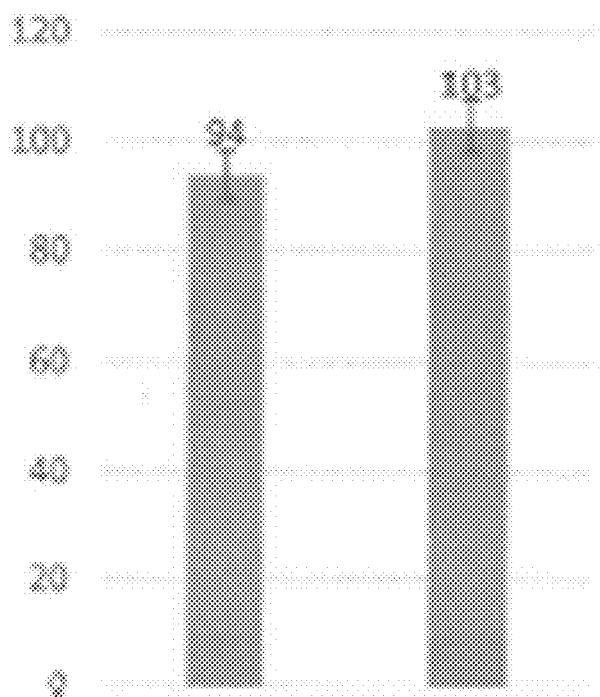
FIG. 9 is a bar graph comparing attachment efficiency (vertical axis), for carriers as described by an Example herein (left bar) vs. a flask (right bar).

Results obtained from the above Examples are provided below with reference to FIGS. 9-12. The efficiency of attachment of the cells to the carriers in the 250 ml bottle was analyzed as described above. FIG. 9 shows a comparison of the efficiency of cell attachment between the 250 ml bottle system and a traditional 175 $cm^2$ flask. Operation of the 250 ml laboratory bottle system included rolling the bottle at 0.2-0.5 RPM on a roller instrument. Attachment efficiency was tested by harvest of the cells 24 hours after seeding.

Figure 10:
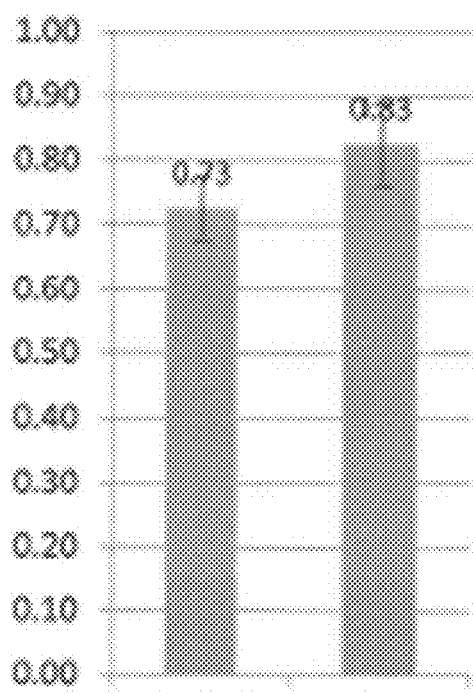
FIG. 10 is a bar graph comparing population-doubling per day (vertical axis), for carriers as described by an Example herein (left bar) vs. a flask (right bar).

It was found that the cells' growth rate in the 250 ml bottle system was slightly less than the growth observed in traditional tissue culture dishes. This is shown in FIG. 10, illustrating a PDD (population-doubling per day) comparison between the 250 ml bottle systems connected to a 2 L reservoir bottle (7 systems) and traditional 175 $cm^2$ flasks.

Figure 11:
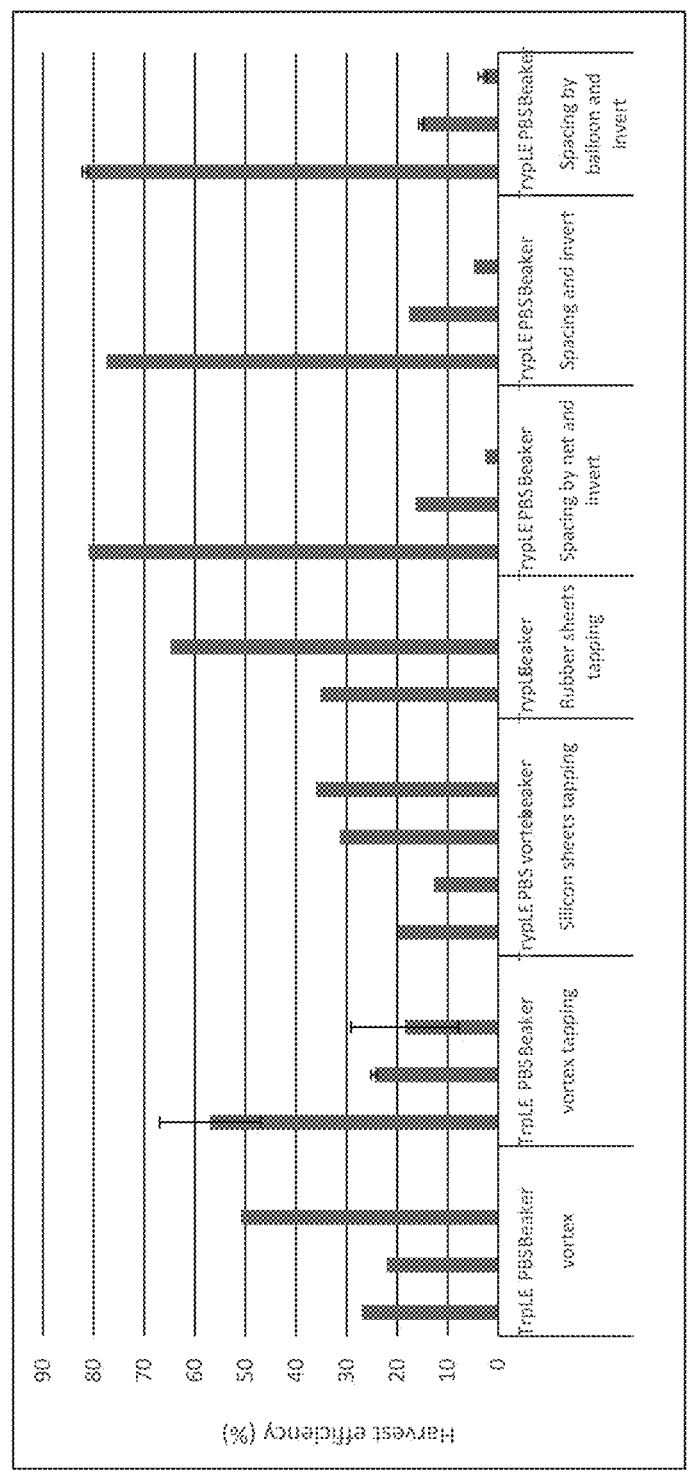
FIG. 11 is a bar graph showing percent of cells harvested (vertical axis), comparing different harvest procedures, as described by an Example herein. Groups shown are after TrypLE incubation ("TrypLE" fraction); washing with PBS ("PBS" fraction); additional manipulations, as described in the text; and/or emptying the carriers into a beaker and rapid mixing ("beaker").
Figure 12:
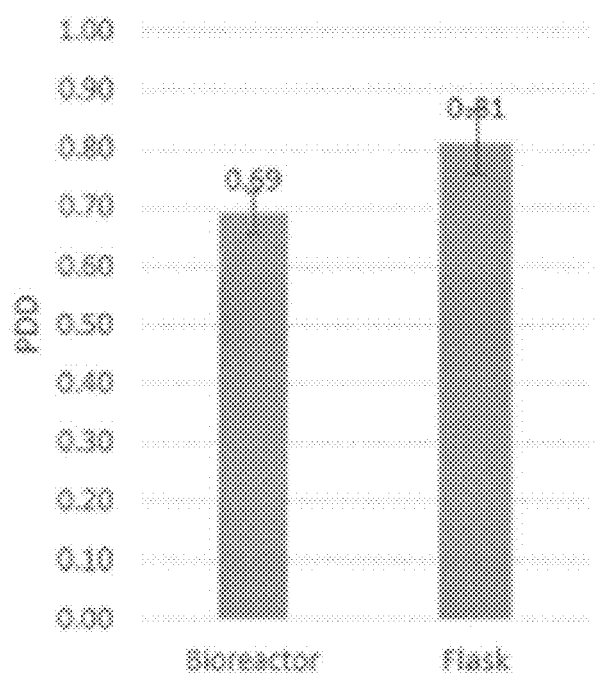
FIG. 12 is a bar graph comparing population-doubling per day (vertical axis), as described by an Example herein.

Different harvest procedures were also tested. The results of these different procedures are shown in FIG. 11. For each procedure, the ability to detach cells was evaluated utilizing the recited harvest element: 1) after TrypLE incubation ("TrypLE" fraction); 2) following washing with PBS ("PBS" fraction); and/or following additional manipulations, as will be described. The rightmost "beaker" bar in each group represents the fraction of cells remaining on the carriers, as assessed by emptying the carriers into a beaker and rapid mixing.

In the first 4 groups, the first two steps (TrypLE incubation and PBS wash) were performed while the carriers were packed tightly. In these groups, the carriers were incubated with TrypLE and conventionally vortexed, then washed with PBS and again conventionally vortexed (leftmost group); a similar procedure was followed, except the vortexing was done by contacting the side of the beaker to the vortex machine (second group); the carriers were mixed by incubation with revolving silicon sheets (third group) or rubber sheets (fourth group). Lastly, the carriers were mixed in a beaker, as described.

In the last 3 groups, the first two steps were performed while the carriers were released from tight packing. In these groups, the carriers were released by moving out the component that formed the wall of the basket, as described in FIG. 13C (fifth group), by opening the basket and transferring the carriers to a different container (sixth group), or initially incubating the carriers with an inflated balloon in the basket and the deflating the balloon (rightmost group). After the carriers were released, the basket was inverted in the presence of TrypLE and/or PBS, followed by mixing the carriers in a beaker, as described.

The procedures that showed the most reliable harvest efficiency were the last three procedures, where the TrypLE incubation and PBS was performed when the carriers were spaced out. Additionally, these procedures also exhibited excellent scalability.

Overall, the rate of cell growth using carriers in a 2.2 L packed-bed New-Brunswick bioreactor was slightly less than the rate of cell growth observed using a traditional flask. This is illustrated by the results shown in FIG. 12, which compares PDD cells growth on carriers in 2.2 L packed-bed New-Brunswick bioreactors and traditional 175 $cm^2$ flasks.

Figure 13A:
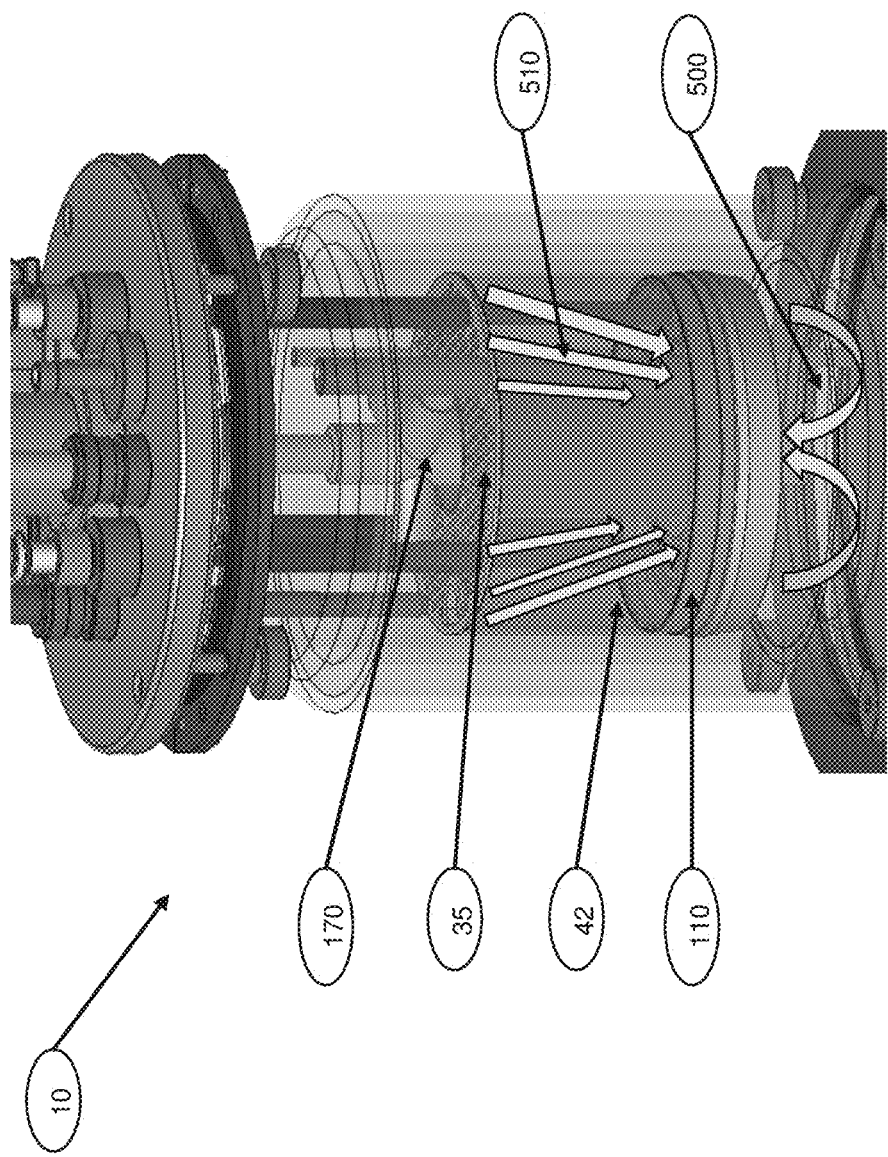
FIG. 13A is a perspective view of a system for growing and harvesting cells in an opened position, according to another exemplary embodiment.

In other embodiments of system 10, with reference to FIG. 13A, carriers may be seeded by introduction of cells (not shown) above component 35. Cells enter middle region 42, containing carriers 30 (not depicted) via upper pores 37. A circulation device such as cell lift impeller 170 creates a vacuum pull 500 below lower component 110, leading to downward fluid flow 510 in middle region 42.

Figure 13B:
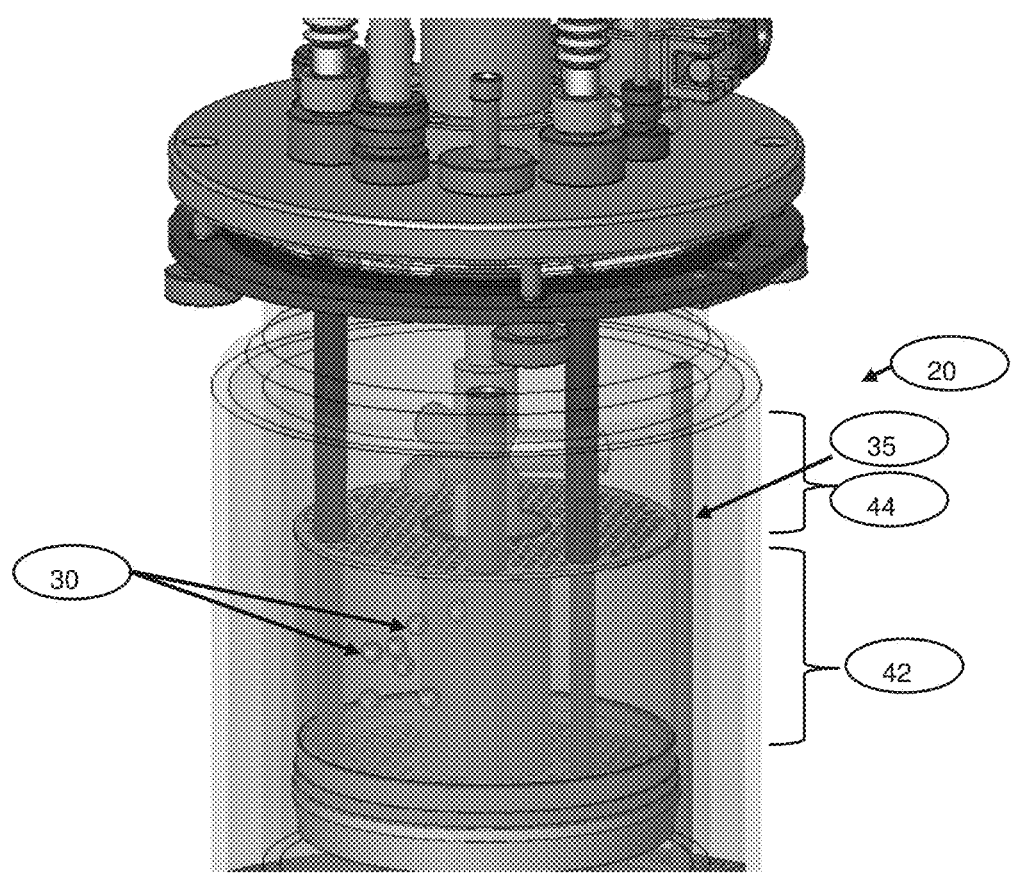
FIGS. 13B-C are perspective views of the system depicted in FIG. 13A, in locked (B) and unlocked (C) configurations.
Figure 13C:
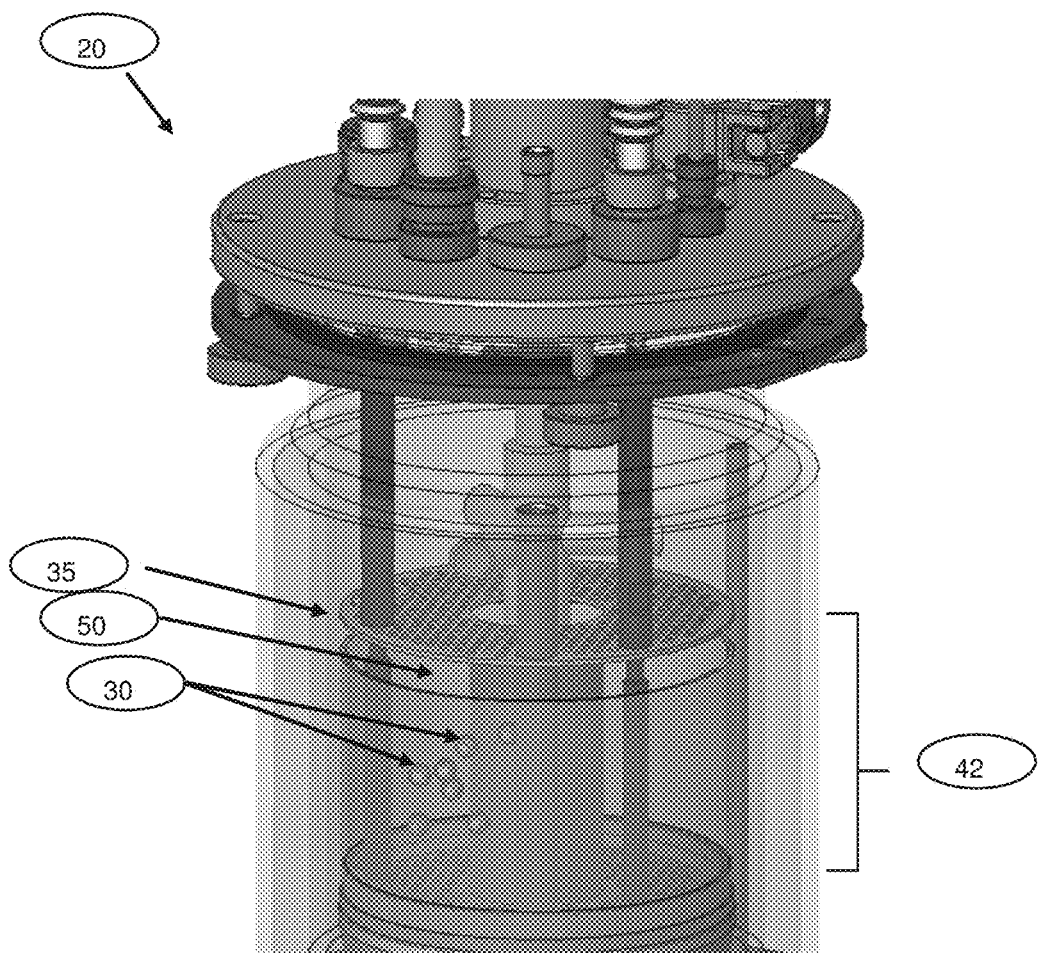

In further embodiments, with reference to FIG. 13B, component 35 may also be locked in a position relative to vessel 20, causing carriers 30 to be tightly packed (not depicted). For example, component 35 may be locked in a first position to create middle region 42 and second region 44 as shown in FIG. 1. In the first position, component 35 may substantial restrict movement of carriers 30 within chamber 40 and confine carriers to middle region 42. In a second position, with reference to FIG. 13C, component 35 may be moved to reduce the volume of second region 44 and increase the volume of middle region 42. In the second position, the volume of middle region 42 includes a headspace 50 above carriers 30. Headspace 50 provides a void volume that carriers 30 may occupy during a harvesting step where carriers 30 are agitated to release cells from carriers.

Figure 14A:
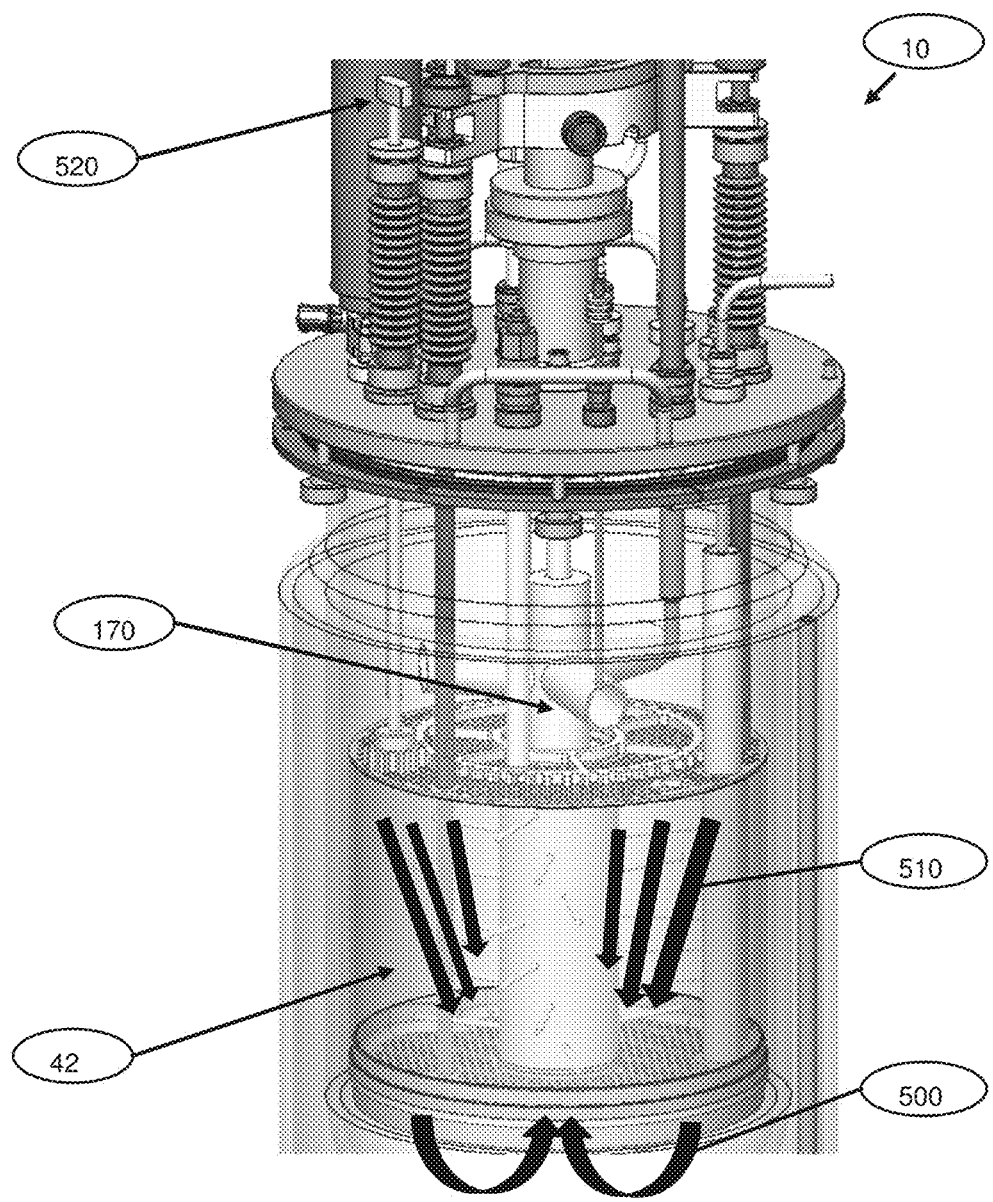
FIG. 14A is a perspective view of a system for growing and harvesting cells in an opened position, according to another exemplary embodiment.
Figure 14B:
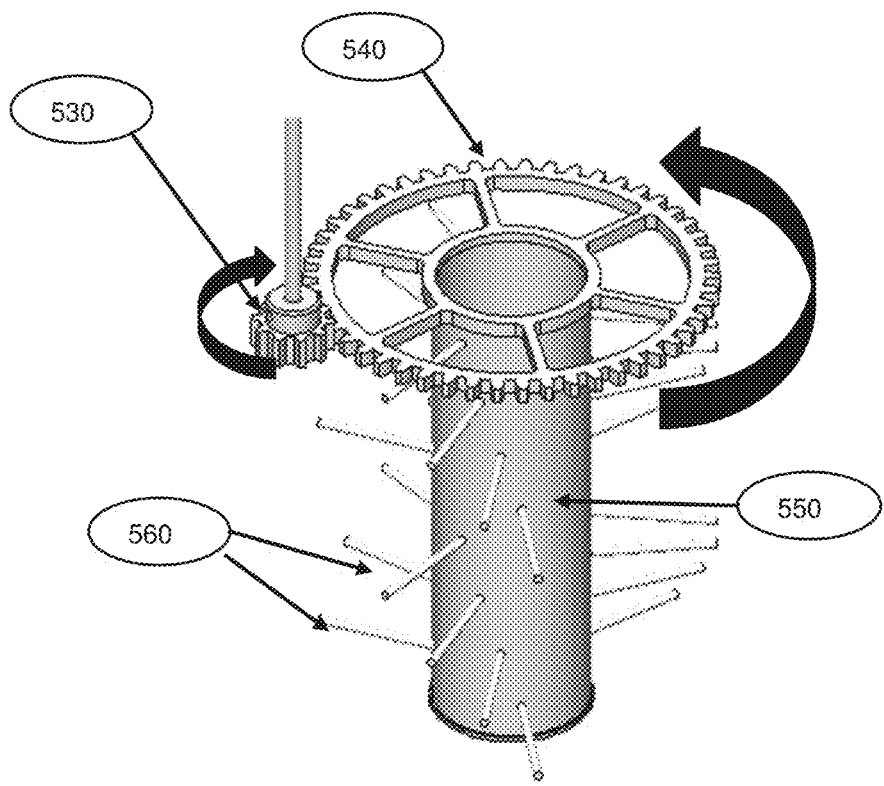
FIG. 14B is a perspective view of a rotating cylinder of the system of FIG. 14A, according to an exemplary embodiment.

In other embodiments of system 10, with reference to FIG. 14A, vessel 20 comprises a rotating cylinder 550, typically along the central axis of vessel 20. Spokes 560 extend radially from rotating cylinder 550 inside middle region 42, enabling mixing of carriers 30 when rotating cylinder 550 is rotated. In certain embodiments, with reference to FIG. 14B, rotating cylinder 550 may be operably connected with an external component capable of transmitting applied torque, such as handle 520, which may optionally be either manually rotatable or connected with a motor (not depicted), via shaft 152. In some embodiments, the operative connection comprises a gear mechanism, including small gear 530 and large gear 540. Rotating cylinder 550 can be used to impart a rotary motion to spokes 560 at the time of and/or after seeding, thus moving carriers 30 in a revolving fashion around middle region 42 and in some cases imparting a degree of spinning motion to carriers 30. This enables a more homogenous distribution of cells in the carriers and increases the efficiency of seeding the carriers, for example as exemplified herein. Rotating cylinder 550 may rotate either in continuous rotary motion, or in other embodiments in a partial rotary motion, for example an oscillating partial rotary motion.

Optionally, cell-lift impeller 170 is also present, creating a vacuum pull 500 below, leading to downward fluid flow 510 in middle region 42. Cell-lift impeller 170 preferably rotates around the same axis as rotating cylinder 550, but is not operably connected with rotating cylinder 550. The term "cell-lift" impeller may refer to an impeller including a vertical tube, whose rotating motion creates a low-differential pressure the base of the tube.

Those skilled in the art will appreciate in light of the present disclosure that seeding of cells in the bioreactor may utilize a variety of conditions that are compatible with cell viability. A non-limiting example of such conditions, for purposes of exemplification only, is 37 deg. C., pH 7.6, and DO concentration of 70%. The speed of rotation of cell-lift impeller 170 may be between 20-150 rotations per minute (rpm), in more specific embodiments between 25-125 rpm, in more specific embodiments between 30-100 rpm, in more specific embodiments between 35-80 rpm, in more specific embodiments between 40-70 rpm, in more specific embodiments between 40-60 rpm, in more specific embodiments about 50 rpm.

The speed of rotation of rotating cylinder 550 during and after seeding may be between 1-50 rpm, in more specific embodiments between 1-40 rpm, in more specific embodiments between 1-30 rpm, in more specific embodiments between 1-20 rpm, in more specific embodiments between 1-15 rpm, in more specific embodiments between 1-10 rpm, in more specific embodiments between 2-10 rpm, in other embodiments between 2-8 rpm, in other embodiments between 2-6 rpm, in other embodiments between 1-8 rpm, or in other embodiments between 1-6 rpm.

The duration of rotation of rotating cylinder 550 during and after seeding may be between 1-24 hr. (hours), in more specific embodiments between 1.5-12 hr., in more specific embodiments between 2-8 hr., in more specific embodiments between 2-6 hr., in more specific embodiments between 2.5-5 hr., in more specific embodiments between 2.5-4 hr., in more specific embodiments between 2.5-3.5 hr., in more specific embodiments about 3 hr. During this time rotating cylinder 550 may be continually rotated, or in other embodiments rotating cylinder 550 may alternate between be stationary and being rotated. As a non-limiting example, rotating cylinder 550 may be rotated 1-6 times per hr., each time for 5-20 seconds, during the first 3 hr. after seeding.

Following the seeding step, carriers 30 are incubated in vessel 20, in the presence of medium, in order to enable cell growth. Typically, the cell-lift impeller will rotate during this time, continuously or intermittently, at rate of 25-200 rpm. Cells that fall through the basket region are, in some embodiments, pulled through the core of the impeller and again seeded at the top of the bioreactor, providing another chance for the cells to adhere to the carriers.

In certain embodiments, at the conclusion of the cell growth phase, rotating cylinder 550 is rotated at a higher speed, for example between 100-400 rpm, in other embodiments 100-350 rpm, in other embodiments 100-300 rpm, in other embodiments 120-300 rpm, in other embodiments 100-250 rpm, in other embodiments 120-250 rpm, in other embodiments 150-250 rpm. This step is preferably performed in the presence of a releasing agent, which may be a protease as described herein.

In other embodiments of system 10, with reference to FIG. 15A, a pump 590 (which may optionally be peristaltic) may be operably connected to vessel 20, via outlet tube 570 and inlet tube 580. Optionally, the outlet tube may feed fluid into a sparger 600 via an internal tube 700 that runs through middle region 42. With reference to FIG. 15B, sparger 600 is typically located under lower component 110 of middle region 42 and may be attached to the underside of lower component 110. With reference to FIG. 15C, when cells are seeded above component 35, the downward fluid flow 510 (not depicted) created by operation of cell-lift impeller 170 can be partially or completely offset by the upward flow 515 created by operation of pump 590, thus slowing or halting the downward passage of cells through middle region 42 and increasing the contact time of cells with carriers.

Figure 16A:
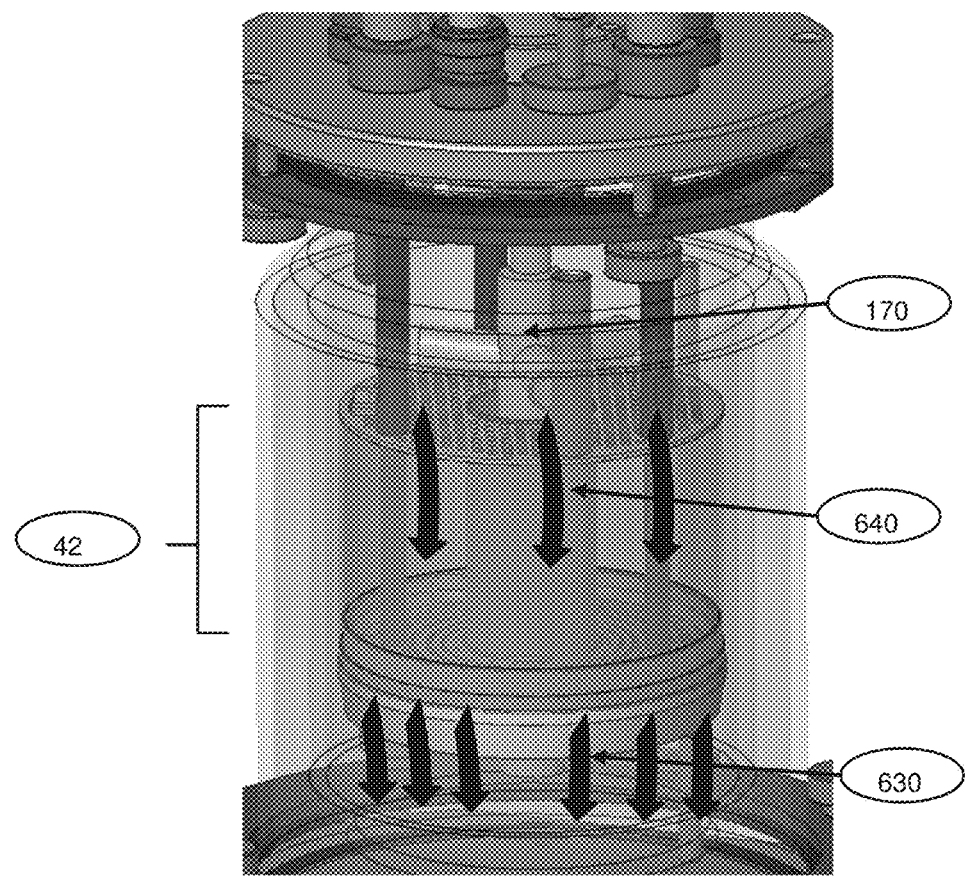
FIG. 16A is a perspective view of a system for growing and harvesting cells in an opened position, according to another exemplary embodiment.

As described above for FIG. 14, operation of cell-lift impeller 170 tends to create a downward fluid flow 510. Since the suction from cell-lift impeller 170 is strongest in the radial center in the region under lower component 110, when lower pores 111 of lower component 110 (also referred to as the "first perforated structure") are of uniform size, the fluid flow is not straight downward but rather in a downward sloping motion inclined towards the center, thus pulling cells towards the center as they move downwards. In certain embodiments of system 10, with reference to FIGS. 16A-C, an altered lower component 610 (FIG. 16C) is disposed at the bottom of middle region 42 (FIG. 16A). Altered lower component 610 contains altered lower pores 615 of varying size. More specifically, altered lower pores 615 increase in diameter at increasing distance from the center of altered lower component 610. The variation of size of altered lower pores 615 partially or completely offsets the pull towards the center by creating a more uniform lower flow 630 through lower component 610, thus generating a more uniform lower pull 640 through middle region 42. In some cases, an O-ring 620 may be present (FIG. 16B). When cells are seeded above component 35, a more homogenous distribution of cells in the carriers and increased efficiency of seeding the carriers are achieved.

In various embodiments, lower pores 615 may have a variety of shapes, including but not limited to substantially circular, irregular in shape, elliptical, polygonal, etc. Lower pores 615 may be characterized by the diameter of the minimal enclosing circle of each pore; which, in the case of a circular pore, corresponds to the diameter of the circles. In certain embodiments, the diameter of the innermost circular row of altered lower pores 615 is typically at least 100 microns, and is, in various embodiments, between 100-2000 microns, between 120-1800 microns, between 120-1500 microns, between 120-1200 microns, between 120-1000 microns, between 150-1800 microns, between 150-1500 microns, between 150-1200 microns, between 150-1000 microns, between 200-1800 microns, between 200-1500 microns, between 200-1200 microns, or between 200-1000 microns. The diameter of the outermost circular row is typically at least 1000 microns, and is, in various embodiments, between 1000-5000 microns, between 1000-4000 microns, between 1000-3000 microns, between 1000-2500 microns, between 1000-2000 microns, between 1200-5000 microns, between 1200-4000 microns, between 1200-3000 microns, between 1200-2500 microns, between 1200-2000 microns, between 1500-4000 microns, between 1500-3000 microns, between 1500-2500 microns, or between 1500-2000 microns.

The ratio of the diameter of the innermost circular row of altered lower pores 615 to the diameter of the outermost circular row of altered lower pores 615 is, in various embodiments, between 1:2 and 1:50; between 1:2 and 1:30; between 1:2 and 1:20; between 1:2 and 1:15; between 1:2 and 1:10; between 1:2 and 1:5; between 1:3 and 1:30; between 1:3 and 1:20; between 1:3 and 1:15; between 1:3 and 1:10; between 1:3 and 1:5; between 1:5 and 1:30; between 1:5 and 1:20; between 1:5 and 1:15; or between 1:5 and 1:10. This disclosure is intended to encompass embodiments where at least some of the circular rows between the innermost circular row and outermost circular row of altered lower pores 615 have an intermediate size, having any number of stepwise increases up to n−1, wherein n is the number of rows; as well as embodiments where there is a binary distribution of pore size.

Figure 16D:
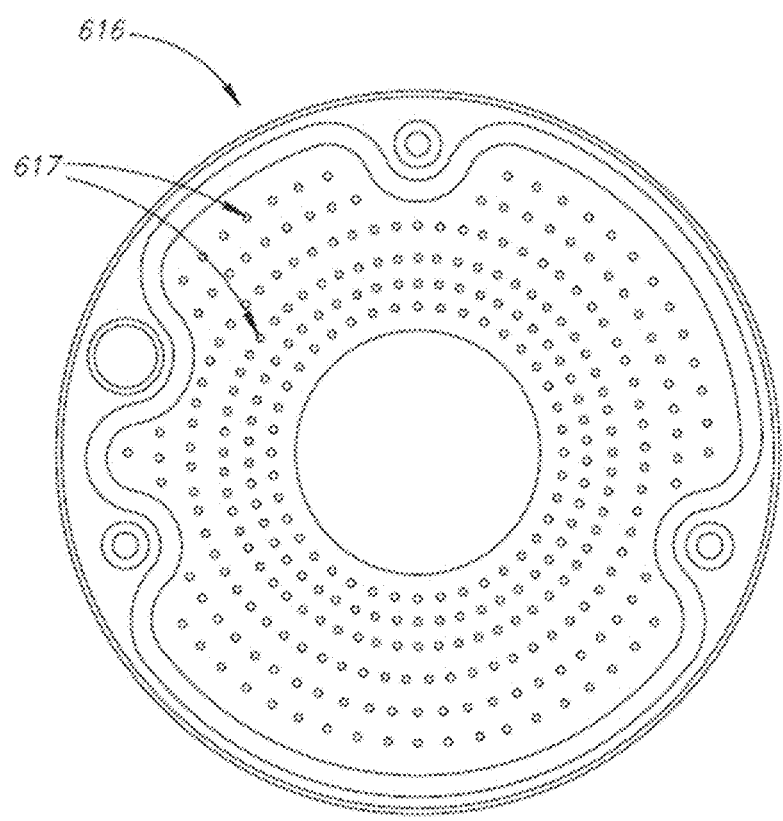
FIG. 16D is a plan view of upper component of the system of FIG. 16A.

Alternatively or in addition, with reference to FIG. 16D, an altered upper component 616 (also referred to as the "second perforated structure") containing altered upper pores 617 is utilized. Upper pores 617 may have a variety of shapes, including but not limited to substantially circular, irregular in shape, elliptical, polygonal, etc. Upper pores 617 may be characterized by the diameter of the minimal enclosing circle of each pore; which, in the case of a circular pore, corresponds to the diameter of the circles. The diameter is relatively small, typically, in various embodiments, at least 100 micron. In other embodiments, the diameter is between 100-2000 microns, between 120-1800 microns, between 120-1500 microns, between 120-1200 microns, between 120-1000 microns, between 150-1800 microns, between 150-1500 microns, between 150-1200 microns, between 150-1000 microns, between 200-1800 microns, between 200-1500 microns, between 200-1200 microns, or between 200-1000 microns. The use of smaller pores serves to decrease the maximum fluid flow rate through altered upper pores 617, thus resulting in regulated downward flow 645. As a result, a more homogenous distribution of cells in the carriers and increased efficiency of seeding the carriers are achieved after cells are seeded above altered upper component 616.

Figure 17B:
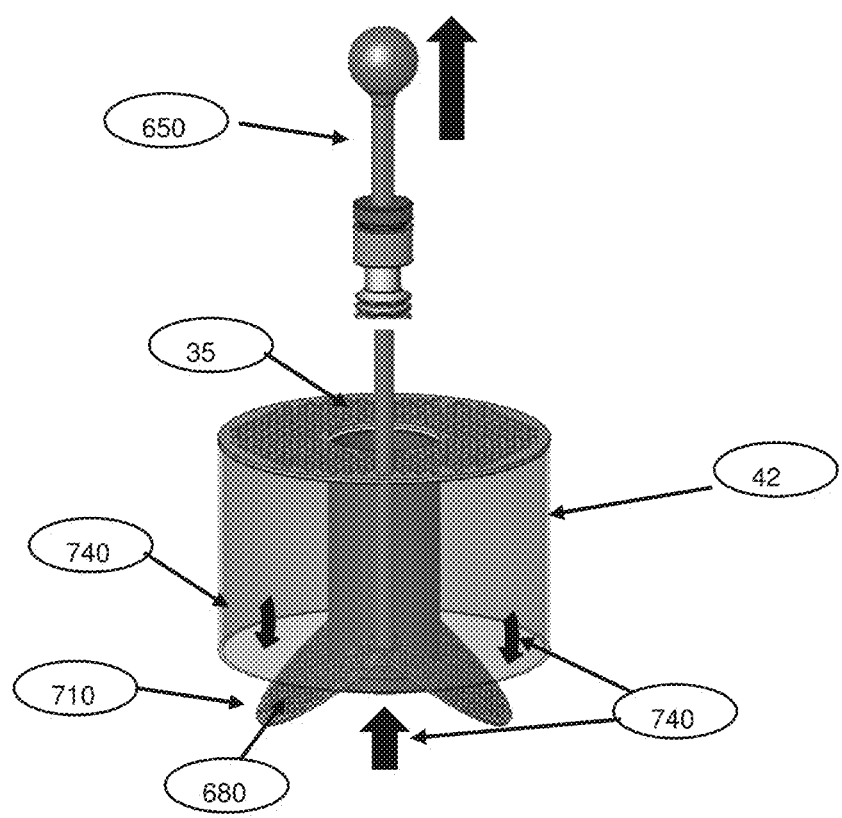
FIG. 17B is a perspective view of a middle region of the system of FIG. 17A.

In other embodiments of system 10, with reference to FIG. 17A, rod 690 extends through upper cover or plate 60 of vessel 20, typically at the central longitudinal axis 153 (not depicted in this Figure) of vessel 20. Rod 690 may be operably connected to a motor (not depicted), for example on top of upper cover or plate 60, or may be magnetic and operably connected to a stirring device (see FIG. 4). Port 70 serves to house rod 690 and is preferably sealed such as to prevent introduction of bacteria or other biological contaminants. Propeller 670 is disposed under folding lower component 680. During the cell growth phase, carriers 30 (not depicted) are disposed in middle region 42, and rod 690 is operably connected with cell growth impeller 170 and is not operably connected with propeller 670. Thus, rotation 720 of rod 690 enables gentle medium circulation via cell growth impeller 170, without a swirling circular motion of medium that would result from rotation of propeller 670. Also present are one or more handles, which may be knobbed handle(s) 650, disposed at the upper end of rod 690, outside (above) upper cover or plate 60, optionally further including bellow 660. With reference to FIG. 17B, at the conclusion of the cell growth phase, pulling knobbed handles 650 (only one of which is depicted in panel B) upward serves to induce folding lower component 680 to assume folded state 710, as shown by directional arrows 740. At the same time, rod 690 may anchor the radial center of lower component 680 (FIG. 17D). This enables carriers 30 to fall from middle region 42 to (lower) third region 46. With reference to FIG. 17C, pushing rod 690 downward serves to engage propeller 670 by operably connecting it with rod 690. With reference to FIG. 17E, at this point rotation of rod 690 effects a swirling circular motion via spinning 730 of propeller 670. Component 35 may remain unaffected by the folding of folding lower component 680.

Spinning 730 of propeller 670 is preferably performed in the presence of a releasing agent, which may be a protease as described herein. In certain embodiments, a slower spinning speed (e.g. 150-200 rpm) is utilized to effect mixing of carriers 30 in wash solution, prior to addition of releasing agent, and a faster spinning speed (e.g. 200-300 rpm) is used in the presence of the releasing agent, in order to release the cells from carriers 30.

In an alternative embodiment, lower component 110 (not depicted), which does not fold, is used in place of folding lower component 680. Cell growth impeller 170 is used to effect both gentle medium circulation and release of cells from carriers 30. Gentle medium circulation utilizes a lower speed, typically 50-150 rpm, while release of cells from carriers 30 utilizes a higher speed, typically 300-500 rpm. Cell growth impeller 170 may also be used during the aforementioned washing step, prior to adding the releasing agent, for example at a speed of 150-200 rpm.

System 10 and small-scale system 310 may, in various embodiments, be used in conjunction with various movable and immobile embodiments of component 35, as an alternative to or freely combined with locking elements 100, bladed impeller 150, stirring device 160, cell-lift impeller 170, altered lower component 610, altered upper component 616, pump 590, and various harvest devices mentioned herein. In other embodiments, any two of these components, any three of these components, any four of these components, any five of these components, any six of these components, or any seven, or more, of these components, are utilized in combination. These aspects may be freely combined with any embodiments of carriers 30.

In certain embodiments, the described systems are used to grow cells on the carriers, but the conditioned medium instead of the cells is the product of interest.

In an experiment, carriers were subjected to plasma treatment prior to their introduction into the bioreactor, using a Tantec VacuLAB machine, available from Tantec (Denmark). The following parameters: time: 30 second (sec); pressure: 2 millibars (mb); air composition: atmospheric. In some cases, following plasma treatment, the carriers were incubated in medium, in this case full DMEM (90% DMEM, 10% FBS, 1% glutamine) for at least 24 hours, prior to introduction into the bioreactor. Both treatments increased the efficiency of cell seeding. Those skilled in the art will appreciate in light of the present disclosure that the parameters of plasma treatment may be varied without abrogating its beneficial effect. For example, the time, pressure, or composition may be varied. Non-limiting variations of the composition include mixtures with higher N2 partial pressure, or with argon or another inert gas such as neon.

In another experiment, the kinetics of cell attachment to placenta-derived adherent stromal carriers in a bioreactor was examined by measuring the percentage of originally-seeded amount of cells still in suspension after 1, 2, and 3 hours. Three hours was sufficient for attachment of the large majority of the cells (FIG. 18).

In another experiment, the effect of stirring the carriers within the basket on seeding was examined by seeding placenta-derived adherent stromal cells with or without stirring and sampling carriers from various regions of the bioreactor. Stirring significantly improved cell dispersion and seeding efficiency (FIG. 19), validating the use of rotating cylinder 550.

In another experiment, the scalability of growth and harvesting in the described bioreactors was examined by growing placenta-derived adherent stromal cells in a 2.2-liter (L) and 5-L bioreactors. The cell density on the carriers and population doubling time, calculated from the number of cells harvested from the reactors were almost indistinguishable between the two bioreactor sizes (see Table below), demonstrating the scalability of the described methods.

TABLE 1

Cell density and population doubling time in 2.2 and 5 L bioreactors.

| Parameter | 2.2 liter bioreactor | 5-L bioreactor |
| --- | --- | --- |
| Carrier cell density | 1100 cells/cm$^2$ | 1170 cells/cm$^2$ |
| Population doubling of cells at harvest | 1.52 | 1.61 |
| Population doubling per day of cells at harvest | 0.38 | 0.40 |

Other embodiments of the disclosure will be apparent to those skilled in the art from consideration of the specification and practice of the present disclosure. It is intended that the specification and examples be considered as exemplary only, with a true scope and spirit of the disclosure being indicated by the following claims.

What is claimed is:

1. A system for growing and harvesting cells, comprising:
   a. a bioreactor comprising a vessel, said vessel comprising a first compartment, said vessel further comprising a second compartment positionable below said first compartment, said second compartment defined between a first perforated structure and a second perforated structure disposed above the first perforated structure, said second perforated structure moveably coupled to the vessel;
   b. a plurality of carriers;
   c. a rod coupled to the second perforated structure, the rod extending upward from the second perforated structure and through a port in an upper plate of the vessel; and
   d. a locking element that engages said upper plate and said rod and locks said second perforated structure in position in said vessel,
   wherein:
      said bioreactor is configured to seed cells in said first compartment, while said plurality of carriers are disposed in said second compartment;
      each of said carriers comprises a body, said body comprising one or more two-dimensional (2D) surfaces extending inwardly from a periphery of the body towards an interior of the body; and
      said bioreactor is configured to incubate said cells together with said carriers in said bioreactor under conditions compatible with growth and survival of said cells.

2. The system of claim 1, wherein when said locking element engages said upper plate and said rod and locks said second perforated structure in position in said vessel, said second perforated structure packs said carriers in said second compartment and prevents movement of said carriers.

3. The system of claim 1, further including an agitation device configured to agitate the carriers in the vessel.

4. The system of claim 1, further comprising a rotating cylinder, having spokes extending radially therefrom, said spokes disposed within said vessel.

5. The system of claim 1, wherein said system is also configured for harvesting said cells at the conclusion of said incubating step, by contacting said carriers with a releasing agent.

6. The system of claim 5, wherein said harvesting further comprises the step of agitating said carriers within said vessel in the presence of said releasing agent.

7. The system of claim 1, wherein said bioreactor further comprises a cell-lift impeller, and said cell-lift impeller is activated during said seeding step.

8. The system of claim 7, wherein said system further comprises a pump that is configured for generating an upward flow of culture media present in the bioreactor vessel during said seeding step.

9. The system of claim 8, wherein the cell-lift impeller generates a downward flow of culture media during said seeding step, wherein the downward flow of culture media is partially or completely offset by the upward flow of culture media.

10. The system of claim 1, wherein said first perforated structure comprises a plurality of pores, wherein pores distal from an inner portion of said first perforated structure are greater in size than pores proximal to the inner portion of said first perforated structure.

11. The system of claim 10, wherein said first perforated structure defines a lower wall of said second compartment.

12. The system of claim 1, wherein said second perforated structure comprises pores having a size in range of 120 microns to 1800 microns in average diameter.

13. The system of claim 12, wherein said second perforated structure defines an upper wall of said second compartment.

14. The system of claim 1, wherein said system is configured for:
   a. manipulating said first perforated structure such that said carriers pass into a third compartment of said vessel, wherein said third compartment is disposed adjacent to said first perforated structure; and
   b. imparting a rotational force to said carriers in said third compartment.

15. The system of claim 14, wherein said first perforated structure folds into a configuration that allows the carriers pass around said first perforated structure from said second compartment into said third compartment of said vessel.

* * * * *